US012703663B2

(12) United States Patent
Røyne et al.

(10) Patent No.: US 12,703,663 B2

(45) Date of Patent: Aug. 11, 2026

(54) BIO-CATALYTIC CALCIUM CARBONATE CEMENTATION

(71) Applicant: Universitetet i Oslo, Oslo (NO)

(72) Inventors: Anja Røyne, Oslo (NO); Alexander Wentzel, Trondheim (NO); Pawel Sikorski, Trondheim (NO)

(73) Assignee: Universitetet i Oslo, Oslo (NO)

( * ) Notice: Subject to any disclaimer, the term of this patent is extended or adjusted under 35 U.S.C. 154(b) by 877 days.

(21) Appl. No.: 16/311,974

(22) PCT Filed: Jun. 23, 2017

(86) PCT No.: PCT/EP2017/065509

§ 371 (c)(1),
(2) Date: Dec. 20, 2018

(87) PCT Pub. No.: WO2017/220768

PCT Pub. Date: Dec. 28, 2017

(65) Prior Publication Data

US 2019/0210924 A1 Jul. 11, 2019

(30) Foreign Application Priority Data

Jun. 24, 2016 (GB) ..................................... 1611065

(51) Int. Cl.

*C04B 28/10* (2006.01)
*C04B 14/06* (2006.01)

(Continued)

(52) U.S. Cl.

CPC .............. *C04B 28/10* (2013.01); *C04B 14/06* (2013.01); *C12N 1/20* (2013.01); *C04B 2111/00646* (2013.01)

(58) Field of Classification Search

CPC . C04B 28/10; C04B 14/28; C04B 2103/0001; C04B 14/06; C04B 2111/00646; C12N 1/20; Y02E 60/13

See application file for complete search history.

(56) References Cited

U.S. PATENT DOCUMENTS 4,617,326 A 10/1986 Bjornberg et al.
5,143,155 A 9/1992 Ferris et al.

(Continued)

FOREIGN PATENT DOCUMENTS

CA 2591097 A1 6/2006
CN 1101626 A 4/1995

(Continued)

OTHER PUBLICATIONS

Kim et al.; Calcium Carbonate Precipitation by Bacillus and Sporosarcina Strains Isolated from Concrete and Analysis of the Bacterial Community of Concrete; J. Microbiol. Biotechnol. (2016), 26(3), 540-548; First published online Dec. 23, 2015 (Year: 2015).*

(Continued)

*Primary Examiner* — Shuangyi Abu Ali

(74) *Attorney, Agent, or Firm* — Tyler Thorp; Newport IP, LLC

(57) ABSTRACT

The present invention is directed to methods of preparing biocement. The methods disclosed herein employ microbial or enzymatic means first to generate acid which dissolves $CaCO_3$, and then to degrade urea, producing $CO_3^-$ ions which increase the pH and lead to the reprecipitation of $CaCO_3$. The precipitation of $CaCO_3$ acts as a cementation process which can bind together particulate materials to yield mortars, concretes and suchlike. The invention further provides construction materials formed by the methods of the invention, and bacterial strains which can be used in the methods of the invention to generate organic acids.

36 Claims, 13 Drawing Sheets

(51) Int. Cl.
*C12N 1/20* (2006.01)
*C04B 111/00* (2006.01)

(56) References Cited

U.S. PATENT DOCUMENTS

| | | | |
|---|---|---|---|
| 7,101,430 B1 | 9/2006 | Pike et al. | |
| 8,182,604 B2 | 5/2012 | Kucharski et al. | |
| 8,420,362 B2 | 4/2013 | Crawford et al. | |
| 8,470,275 B2 | 6/2013 | Constantz et al. | |
| 8,518,177 B2 | 8/2013 | Chattopadhyay et al. | |
| 8,728,365 B2 | 5/2014 | Dosier | |
| 8,932,400 B2 | 1/2015 | Chen et al. | |
| 8,951,786 B1 * | 2/2015 | Dosier | C04B 24/126 435/289.1 |
| 9,199,880 B2 | 12/2015 | Dosier | |
| 9,428,418 B2 | 8/2016 | Dosier | |
| 9,796,626 B2 | 10/2017 | Dosier | |
| 10,450,695 B2 | 10/2019 | Dosier et al. | |
| 10,626,547 B2 | 4/2020 | Dosier et al. | |
| 10,717,674 B2 | 7/2020 | Hill et al. | |
| 11,008,591 B2 | 5/2021 | Dosier et al. | |
| 2008/0245272 A1 | 10/2008 | Kucharski et al. | |
| 2010/0086367 A1 | 4/2010 | Darson-Baulleur et al. | |
| 2011/0027850 A1 | 2/2011 | Crawford et al. | |
| 2011/0262640 A1 | 10/2011 | Dosier | |
| 2013/0196419 A1 | 8/2013 | Chavez Crooker et al. | |
| 2014/0239535 A1 | 8/2014 | Dosier | |
| 2015/0322604 A1 | 11/2015 | Brunner et al. | |
| 2016/0068438 A1 | 3/2016 | Dosier | |
| 2016/0264463 A1 | 9/2016 | Dosier et al. | |
| 2016/0362334 A1 | 12/2016 | Dosier | |
| 2017/0190617 A1 | 7/2017 | Hill et al. | |
| 2018/0118623 A1 | 5/2018 | Smith et al. | |
| 2018/0244585 A1 | 8/2018 | Rahbar et al. | |
| 2018/0305858 A1 | 10/2018 | Dosier et al. | |
| 2019/0106716 A1 | 4/2019 | Dosier et al. | |
| 2019/0106717 A1 | 4/2019 | Dosier et al. | |
| 2020/0171533 A1 | 6/2020 | Dosier et al. | |
| 2020/0262711 A1 | 8/2020 | Dosier et al. | |
| 2020/0331804 A1 | 10/2020 | Hill et al. | |
| 2020/0346976 A1 | 11/2020 | Hill et al. | |
| 2021/0189238 A1 | 6/2021 | Kavazanjian et al. | |
| 2021/0395146 A1 | 12/2021 | Dosier et al. | |
| 2022/0126317 A1 | 4/2022 | Dosier et al. | |
| 2023/0383316 A1 | 11/2023 | Dosier | |
| 2024/0343598 A1 | 10/2024 | Dosier | |

FOREIGN PATENT DOCUMENTS

| | | |
|---|---|---|
| CN | 1125472 A | 6/1996 |
| CN | 1778934 A | 5/2006 |
| CN | 101270369 A | 9/2008 |
| CN | 102121033 A | 7/2011 |
| CN | 103173376 A | 6/2013 |
| CN | 103173376 B | 10/2014 |
| CN | 104071890 A * | 10/2014 |
| EP | 1838642 A1 | 10/2007 |
| EP | 1893546 A1 | 3/2008 |
| EP | 2429970 A1 | 3/2012 |
| EP | 2940122 | 11/2015 |
| EP | 3239299 | 11/2018 |
| JP | 2008524096 A | 7/2008 |
| JP | 5284646 B2 | 9/2013 |
| WO | WO-2006066326 A1 | 6/2006 |
| WO | 2008/009771 | 1/2008 |
| WO | WO-2008120979 A1 | 10/2008 |
| WO | WO-2010130712 A1 | 11/2010 |
| WO | WO-2011137106 A1 | 11/2011 |
| WO | WO-2016145190 A1 | 9/2016 |
| WO | WO-2017189106 A1 | 11/2017 |
| WO | WO-2018064320 A1 | 4/2018 |
| WO | WO-2018081542 A1 | 5/2018 |
| WO | WO-2018200684 A1 | 11/2018 |
| WO | WO-2019071172 A1 | 4/2019 |
| WO | WO-2019071175 A1 | 4/2019 |

OTHER PUBLICATIONS

EP Communication Pursuant to Article 94(3) EPC, pertaining to co-pending EP Application No. 17732127.0, dated Feb. 27, 2020—5 Pages.

International Search Report dated Sep. 19, 2017, in co-pending PCT International Application No. PCT/EP2017/065509—4 Pages.

Written Opinion dated Sep. 19, 2017, in co-pending PCT International Application No. PCT/EP2017/065509—7 Pages.

European Search Report based on co-pending Great Britain Application No. GB1611065.2, dated Jan. 13, 2017, 6 Pages.

Achal, Varenyam, et al., "Biogenic Treatment Improves the Durability and Remediates the Cracks of Concrete Structures", Construction and Building Materials, 2013, vol. 48, pp. 1-5.

BioZEment—UiO Department of Physics, downloaded from internet as http://www.mn.uio.no/fysikk/english/research/groups/pgp/research/carbonates and co . . . printed Sep. 6, 2016—2 Pages.

Choi, Sun-Gyu, et al., "Biocementation for Sand Using an Eggshell as Calcium Source", Journal of Geotech, Journal of Geotechnical and Geoenvironmental Engineering, Technical Note, 2016, pp. 1-4.

Choi, Sun-Gyu, et al., "Properties of Biocemented, Fiber Reinforced Sand", Construction and Building Materials, 2016, vol. 120, pp. 623-629.

Chu, Jian, "Solutions to Sustainability in Construction: Some Examples", Procedia Engineering, 2016, vol. 145, pp. 1127-1134.

Chu, Jian, et al., "Proof of Concept: Biocement for Road Repair", Final Report, Mar. 2015, Iowa State University, Midwest Transportation Center, 15 Pages.

Cunningham, A.B., et al., "Reducing the Risk of Well Bore Leakage of CO2 Using Engineered Biomineralization Barriers", Energy Procedia, 2011, vol. 4, pp. 5178-5185.

Fujita, Yoshiko, et al., Evaluating the Potential of Native Ureolytic Microbes to Remediate a 90Sr Contaminated Environment, Environmental Science & Technology, 2010, vol. 44, No. 19, pp. 7652-7658.

Ghosh, P., et al., "Use of Microorganism to Improve the Strength of Cement Mortar", Cement and Concrete Research, 2005, vol. 35, pp. 1980-1983.

Jonkers, Henk M., et al., "A Two Component Bacteria-Based Self-Healing Concrete", Concrete Repair, Rehabilitation and Retrofitting II, 2009, pp. 119-120.

Phula, Y.J., et al., "Morphology and Polymorphism of Calcium Carbonate Precipitated from Different Calcium Sources Via Enzyme Induced Carbonate Precipitation", Department of Physics, University of Oslo, Norway, 2016, Goldschmidt Conference Abstracts—1 Page.

Rodriguez-Navarro, Carlos, et al., "Influence of Substrate Mineralogy on Bacterial Mineralization of Calcium Carbonate: Implications for Stone Conservation", Applied and Environmental Microbiology, Jun. 2012, vol. 78, No. 11, pp. 4017-4029.

Stabnikov, Viktor, et al., "Halotolerant, Alkaliphilic Urease-Producing Bacteria from Different Climate Zones and their Application for Biocementation of Sand", World Journal of Microbiology and Biotechnology, 2013, vol. 29, pp. 1453-1460.

Van Paassen, Leon A., et al., "Potential Soil Reinforcement by Biological Denitrification", Ecological Engineering, 2010, vol. 36, pp. 168-175.

Zander, R., et al., "Association Between Plasma lonized Calcium and Lactate Concentration", Intensive Care Medicine, 1993, vol. 19, No. 6, pp. 362-363.

Becker, Karsten, et al., "Coagulase-Negatice *Staphylococci*", Clinical Microbiology Reviews, Oct. 2014, vol. 27, No. 4, pp. 870-926.

Byappanahalli, Muruleedhara N., et al., "Enterococci in the Environment", Microbiology and Molecular Biology Reviews, Dec. 2012, vol. 76, No. 4, pp. 685-706.

Kim, Ji Hyung, et al., "First Report of Human Acute Acalculous Cholecystitis Caused By The Fish Pathogen *Lactococcus garvieae*", Journal of Clinical Microbiology, Feb. 2013, vol. 51, No. 2, pp. 712-714.

BioZEment (completed). Web Page. UiO Department of Physics. Published Nov. 3, 2014. Last modified Nov. 27, 2017. Retrieved Oct. 22, 2021 at URL: https://www.mn.uio.no/fysikk/english/research/projects/biozement/. 5 pages.

(56) References Cited

OTHER PUBLICATIONS

Castro-Alonso et al., Microbially Induced Calcium Carbonate Precipitation (MICP) and Its Potential in Bioconcrete: Microbiological and Molecular concepts. Frontiers in Materials, 2019, vol. 6, Article 126: 1-15.
Co-pending U.S. Appl. No. 16/933,171, inventors Hill; Thomas A et al., filed Jul. 20, 2020.
Cree et al. Sustainable Bio-Inspired Limestone Eggshell Powder for Potential Industrialized Applications. ACS Sustainable Chem Eng 3, 941-949 (Apr. 9, 2015).
Cuzman et al., Bacterial "Masons" at work with wastes for producing eco-cement. Int. J. Environ. Sci. Develop., 2015, vol. 6(10): 767-774.
De Muynck, Willem et al, Microbial Carbonate Precipitation in Construction Materials: A Review, Ecological Engineering, 2010, pp. 118-136, vol. 36, Elsevier.
Dejong, Jason T. et al, Bio-mediated Soil Improvement; Ecological Engineering, 2009, pp. 197-210, vol. 36, Elsevier.
Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.
Hammes et al. Key roles of pH and calcium metabolism in microbial carbonate precipitation. Re/Views in Environmental Science & Bio/Technology 1:3-7 (2002).
Ivanov et al., Chapter 7, Biocementation and Biocements. Construction Biotechnol., Green Energy and Technol., Chapter 7, 2017, pp. 109-138.
Ivanov et al. Sustainable and Safe Construction Biomaterials: Biocements and Biogrouts. Frontiers in Biomaterials, vol. 6, pp. 177-193 (2019).
Kurizaki et al, "A Case of Stone Formation in the Mainz Pouch using Appendix as the Efferent Limb: A Case Report", Nihon Hinyokika Gakkai Zasshi. The Japanese Journal of Urology, 2002, vol. 93(4), pp. 573-576. (English translation of abstract.).
PCT/EP2017/065509 International Preliminary Report on Patentability dated Dec. 25, 2018.
Phillips et al., Engineered applications of ureolytic biomineralization: a review. Biofouling, 2013, vol. 29(6): 715-733.
Reddy et al. Embodied energy of common and alternative building materials and technologies. Energy and Buildings, vol. 35, Issue 2, pp. 129-137 (2003).
Stocks-Fischer, Shannon et al, Microbiological Precipitation of CaCO3, Soil Biology and Biochemistry, 1999, pp. 1563-1571, vol. 31, Elsevier Science Ltd.
The Better Brick, 2010 Next Generation Winner (https://www.metropolismag.com/uncategorized/the-better-brick-2010-next-generation-winner/).
Through the Sandglass, (http://throughthesandglass.typepad.com/through_the_sandglass/2010/07/sandbacteriaurinebricks-continuing-performances-of-bacillus-pasteurii.html) Jul. 19, 2010.
Wang et al., Application of microorganisms in concrete: a promising sustainable strategy to improve concrete durability. Appl. Microbial Biotechnol., 2016, vol. 100: 2993-3007.
Whiffin. Victoria S. et al, Microbial Carbonate Precipitation as a Soil Improvement Technique, Geomicrobiology Journal, 2007, pp. 417-423, vol. 24, Taylor & Francis Group, LLC.
Whiffin, Victoria S., Microbial CaCO3 Precipitation for the Production of Biocement, PhD Thesis, 2004, Murdoch University, Western Australia.
"Foreign Office Action", CA Application No. 3,028,840, mailed on Jul. 29, 2024, 4 pages.
Communication pursuant to Article 94(3) EPC, Received for European Application No. 20755659.8, mailed on Sep. 19, 2024, 3 pages.
Notification No. 134030-SHTT-SC, Received for Vietnamese Application No. 1-2021-05730, mailed on Dec. 31, 2024, 2 pages.
"Foreign Office Action", BR Application No. BR1120210161970, mailed on Feb. 12, 2025, 7 pages.
"Foreign Office Action", KR Application No. 10-2021-7029728, mailed on Mar. 11, 2025, 7 pages.
"Foreign Office Action", CA Application No. 3, 130,264, mailed on Jun. 2, 2025, 5 pages.
"Foreign Office Action", IL Application No. 285616, mailed on Jan. 12, 2024, 5 pages.
"Foreign Office Action", UAE Application No. P6001439/21, mailed on Oct. 20, 2024, 9 pages.
"Foreign Office Action", JP Application No. 2021-547827, mailed on Oct. 29, 2024, 4 pages.
"Foreign Office Action", CN Application No. 202310978752.4, mailed on Jul. 15, 2025, 11 pages.

* cited by examiner

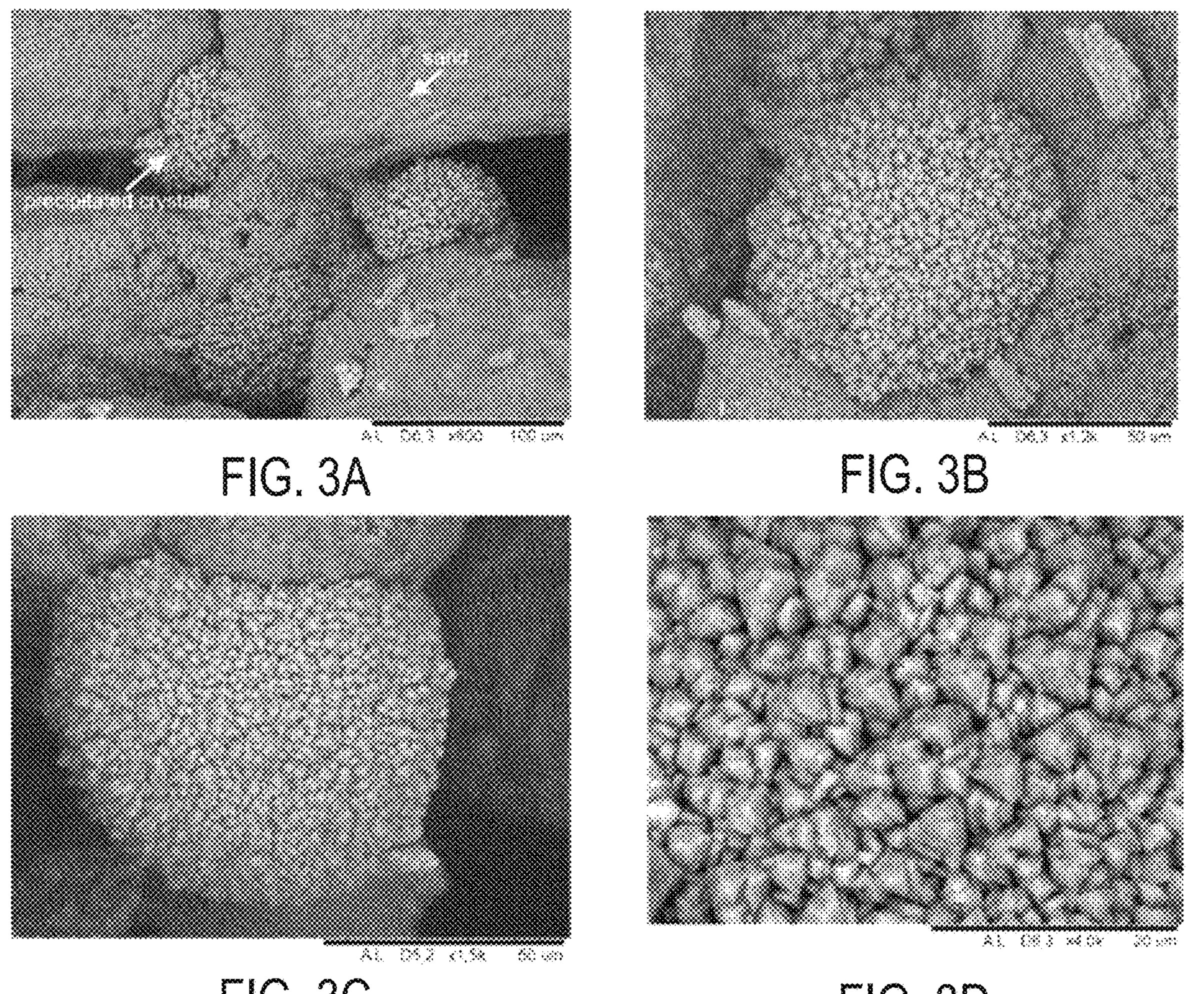
FIG. 3A
FIG. 3B
FIG. 3C
FIG. 3D
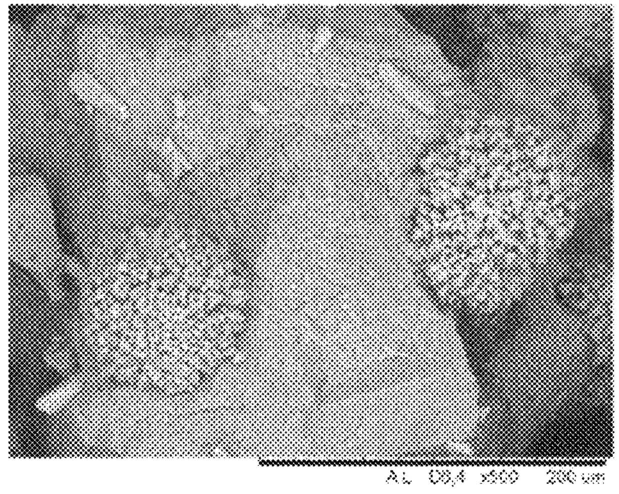
FIG. 4

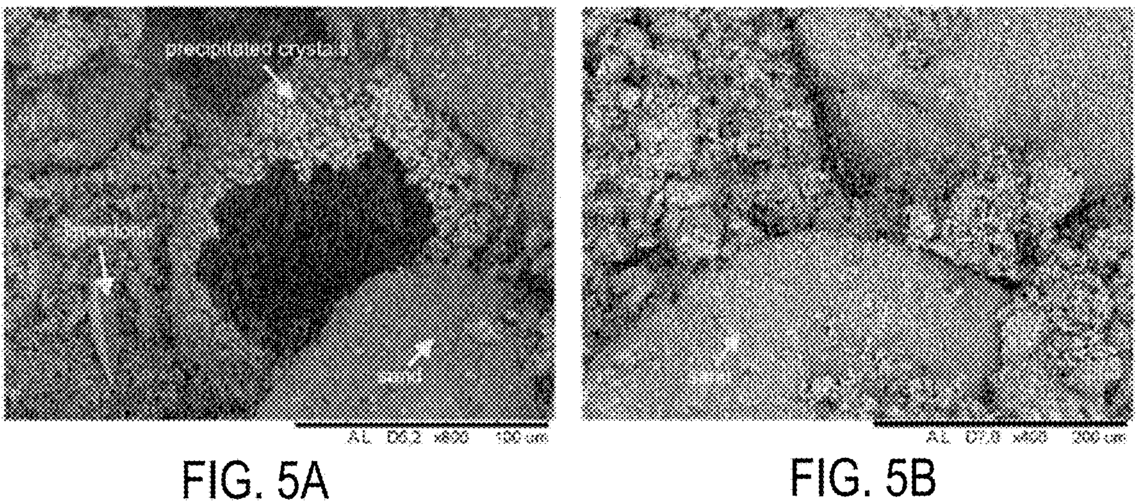
FIG. 5A
FIG. 5B
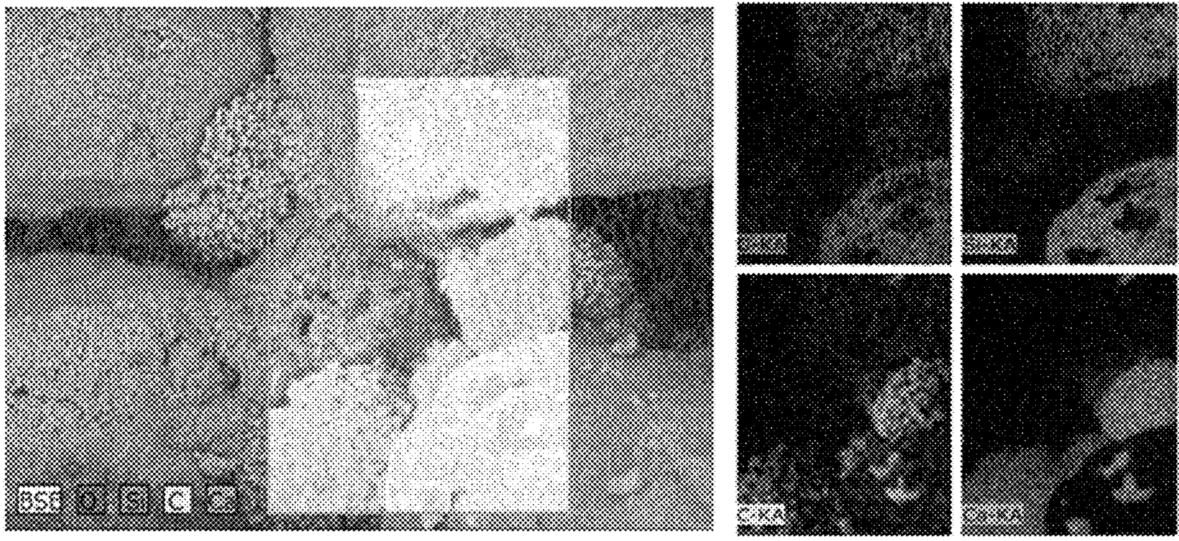
FIG. 6

BIO-CATALYTIC CALCIUM CARBONATE CEMENTATION

CROSS-REFERENCE TO RELATED APPLICATIONS

This application is a national stage application filed under 35 U.S.C. § 371 of PCT/EP2017/065509, filed Jun. 23, 2017, which claims the benefit of Great Britain Application No. 1611065.2, filed Jun. 24, 2016, and Great Britain Application No. 1701821.9, filed Feb. 3, 2017, each of which is incorporated herein, in its entirety, by reference.

The present invention relates to a new process for preparing cement and cement-based products, and in particular a construction material based on or comprising a calcium carbonate cement, wherein enzymatic processes are used to generate changes in pH which induce dissolution and subsequently precipitation, or recrystallization, of calcium carbonate, thereby to render it functional as a cement. The calcium carbonate cement (precipitated/recrystallized calcium carbonate) is used to bind together a particulate starting material to form a construction material. Advantageously the pH changes may be generated through the metabolic activity of microorganisms, particularly bacteria. The invention also provides novel bacteria suitable for such use and construction materials obtained by the methods of the invention.

Cement is an important component in the construction industry. It is normally used as a binder in binding other materials together, and also as a component of mortar for masonry. The cement industry accounts for approximately 5% of worldwide man-made carbon dioxide ($CO_2$) emissions, of which 50% is from the chemical process of cement production itself (the conversion of calcium carbonate ($CaCO_3$) to calcium oxide (CaO)), and 40% from burning fuel to obtain the high temperatures required for the process to take place. For example, Portland cement and magnesium cement are produced by heating crushed limestone at 1450° C. and 750° C., respectively. These processes thus not only inherently emit a lot of $CO_2$, but also involve high energy consumption and the associated further high levels of $CO_2$ emission.

Due to increased environmental awareness, numerous approaches have been introduced in recent years in order to minimize the environmental impact of the cement industry. One of the most effective methods of reducing emissions and energy use in cement production today is to replace a portion of the Portland cement with pozzolanic materials of natural (volcanic) or industrial (fly ash, blast furnace slag) origin. New cement materials such as energetically modified cement and bio-cement have also been introduced over the last few decades, in an effort to reduce the energy consumption and environmental pollution associated with cement production by the use of alternative routes.

Bio-cement is a material that is produced via a biological approach. To date, the most commonly reported system of bio-cement is the use of ureolytic bacteria which can produce a urease enzyme (U.S. Pat. No. 8,728,365). The urease enzyme then hydrolyses urea provided in the system to form carbonate ions, which react with provided calcium ions to form insoluble calcium carbonate ($CaCO_3$). Cementation is achieved by the precipitation of $CaCO_3$. This mechanism is known as microbial induced carbonate precipitation (MICP). Studies of MICP are abundant, and aim to use it for a variety of different applications, including stone conservation (Rodriguez-Navarro, C. et al., Applied and Environmental Microbiology, 2012. 78(11): pp. 4017-4029), crack remediation in concrete (Achal, V. et al., Construction and Building Materials, 2013. 48: pp. 1-5), cement mortar (Ghosh, P. et al., Cement and Concrete Research, 2005. 35(10): pp. 1980-1983), soil stabilization (van Paassen, L. A. et al., Ecological Engineering, 2010. 36(2): pp. 168-175), self-healing concrete (Jonkers, H. M. and Schlangen, E., Concrete Repair, Rehabilitation and Retrofitting II, 2009, pp. 119-120, Taylor & Francis Group, London), contaminant adsorption and immobilization (Fujita, Y. et al., Environmental Science & Technology, 2010. 44(19): pp. 7652-7658) and construction of subsurface barriers against pollutant spread or reservoir leakage (Cunningham, A. B. et al., Energy Procedia, 2011. 4: pp. 5178-5185), etc. The great potential of bio-cement as a greener alternative to traditional cements is demonstrated by the use of the concept by several companies, for instance by Calcite Bioconcept (France), who use an MICP approach for the surface treatment of stonework, and by bioMASON Inc., which employs natural microorganisms and chemical processes to manufacture biological cement-based masonry building materials.

Though bio-cement is, in environmental terms, a great improvement on more traditional cements such as Portland cement, there remains the issue that calcium ions must be added to the mix for the formation of $CaCO_3$. These are generally added in the form of a calcium chloride solution (U.S. Pat. Nos. 8,728,365, 8,951,786), although other calcium salts such as calcium nitrate may also, or additionally be used. Calcium chloride is generally obtained as a by-product of the Solvay process, which has the overall formula:

$$2NaCl+CaCO_3 \rightarrow Na_2CO_3+CaCl_2$$

Thus calcium is obtained initially from $CaCO_3$, added to the bio-cement mix in the form of $CaCl_2$ and then precipitates out as $CaCO_3$ again. The inventors of the present application have designed a significantly improved method of producing bio-cement whereby the calcium ions are obtained directly from $CaCO_3$, by dissolving $CaCO_3$ in acid, based on the following reaction using lactic acid as an example (although another acid may be used in an analogous reaction):

$$CaCO_3+\text{lactic acid(Hlac)} \rightarrow Ca^{2+}+HCO_3^-+Lac^-$$

The calcium (and carbonate) ions can then be used in a process akin to a traditional bio-cementation process: hydrolysis of urea yields carbonate in the following reaction:

$$(NH_2)_2CO+3H_2O \rightarrow 2NH_4^++HCO_3^-+OH^-$$

In the traditional process, hydrolysis of urea is used to generate carbonate ions for synthesis of the calcium carbonate. However, according to the present invention the urea hydrolysis reaction is used in a different way: this reaction causes an increase in pH, causing the $CaCO_3$ previously dissolved in acid (as described above) to re-precipitate, according to the reaction:

$$Ca^{2+}+HCO_3^-+OH^- \rightarrow CaCO_3+H_2O$$

solidifying the cement. Thus, the production of carbonate is not necessary as a result of this reaction, and other enzymatic reactions which generate, or result in an increase in pH, may alternatively be employed, such as for example enzymatic reactions which use, or consume, acid as a substrate. As is normal in the art, by performing such a reaction in the presence of a loose aggregate or particulate material, the precipitated $CaCO_3$ will bind the aggregate or particles together, yielding a composite material. Such a composite material is a construction material, such as a concrete or mortar.

Particularly advantageously, the inventors have isolated novel strains of bacteria from sites near a limestone quarry in Tromsdalen, Norway, which may be used in this process. A large number of such strains have been obtained and certain of these, whose species have not yet been identified or confirmed and may be previously unknown, have been deposited at the NCIMB (UK), which is located at the following address: Ferguson Building, Craibstone Estate, Bucksburn, Aberdeen AB21 9YA. Five strains have been deposited, known as AP-004, AP-006, AP-029, AP-044 and UP-009. These strains were all deposited by the applicant on 22 Jun. 2016, and have the following accession numbers:

AP-004-42596;
AP-006-42597;
AP-029-42598;
AP-044-42599; and
UP-009-42600.

These strains are able to produce high levels of acid, particularly lactic acid, sufficient to dissolve $CaCO_3$ to yield calcium ions, and may thus be used in the first step of the process. These strains offer a distinct technical advantage with regard to acid production over previously-known strains, as no commercially-available strain which was screened was found to produce sufficient acid under appropriate conditions to be used in this method, unlike the newly-isolated strains listed above. The method of the application thus enables the bio-production of calcium ions directly from $CaCO_3$, cutting out the need for the chemical production of $CaCl_2$ (or other calcium salts) in the process. By cutting out this production step, the method of the application significantly reduces the environmental footprint of the cement. The Solvay Process, whereby $CaCl_2$ is produced, is highly energetically costly, requiring the heating of $CaCO_3$ to temperatures of 950-1100° C. By cutting out this step, the method of the invention significantly reduces the environmental impact of bio-cement.

Thus, in a first aspect, the invention provides a method of forming a construction material from $CaCO_3$ and a particulate starting material, said method comprising:

(i) enzymatically generating an acid in a $CaCO_3$-containing preparation to decrease the pH of said preparation, thereby dissolving at least a part of the $CaCO_3$ to produce a dissolved calcium carbonate preparation (DCCP);

(ii) combining the DCCP with a particulate starting material; and (iii) enzymatically generating an increase in the pH of said combined mixture of (ii) thereby causing at least a part of the dissolved $CaCO_3$ to precipitate and to bind together at least part of the particulate starting material and precipitated $CaCO_3$, and optionally a part of any undissolved $CaCO_3$, to form the construction material;

wherein the $CaCO_3$ and the particulate starting material may be separate or pre-mixed prior to (i), such that in step (ii) the combination of the DCCP with the particulate starting material may take place simultaneously with or after the production of the DCCP, and wherein one or more of the reagents for enzymatically increasing the pH in step (iii) may be present in the $CaCO_3$-containing preparation, or may be added during or after any one of steps (i) or (ii), or in step (iii).

In a second aspect, the invention provides a construction material formed by the method of the first embodiment.

In a third aspect, the invention provides a method of forming a cement from $CaCO_3$, said method comprising:

(i) enzymatically generating an acid in a $CaCO_3$-containing preparation to decrease the pH of said preparation, thereby dissolving at least a part of the $CaCO_3$ to produce a dissolved calcium carbonate preparation (DCCP);

(ii) optionally combining the DCCP with a particulate material; and (iii) enzymatically generating an increase in the pH of said DCCP or said combined mixture of (ii) thereby causing at least a part of the dissolved $CaCO_3$ to precipitate to form a cement, wherein the precipitated $CaCO_3$ is able to function as a cement to bind together particulate or other construction materials;

wherein where the method comprises step (ii) the $CaCO_3$ and the particulate material may be separate or pre-mixed prior to (i), such that in step (ii) the combination of the DCCP with the particulate material may take place simultaneously with or after the production of the DCCP, and wherein one or more of the reagents for enzymatically increasing the pH in step (iii) may be present in the $CaCO_3$-containing preparation, or may be added during or after any one of steps (i) or (ii), or in step (iii).

Advantageously, in the methods of the invention the enzymes for the steps of enzymatically generating a decrease or increase of pH may be provided in the form of a microorganism or microbial extract.

Further aspects of the invention provide use of a cement prepared according to the method of the invention, as defined above, to connect construction materials, such as masonry units, together, and a method of connecting construction materials together, said method comprising applying a cement prepared according to the method of the invention, as defined above, to at least one construction material unit and placing it together with at least one other construction material unit.

In a still further aspect, the invention provides a bacterium suitable for use in in the methods of the invention, more particularly for the production of acid in the methods, said bacterium being:

(i) alkaliphilic;

(ii) able to produce acid under aerobic conditions at a pH of at least 8.5 (particularly in the presence of $CaCO_3$, e.g. limestone, and more particularly also under low oxygen conditions); and (iii) able to dissolve $CaCO_3$ to produce $Ca^{2+}$ ions, (particularly in the presence of glucose and $CaCO_3$).

In one preferred embodiment the bacterium is capable of forming spores. The invention also provides a bacterium as deposited at the NCIMB under accession number 42596, 42597, 42598, 42599, 42600, or a mutant or modified strain thereof.

In particular, such a mutant or modified strain will have the identifying characteristics of the parent bacterium from it is derived. Most notably, the mutant or modified strain will have the properties listed above. The mutant or modified strain may be a genetically engineered variant of a deposited bacterium, and/or it may have been obtained through mutagenesis (random or directed) or adaptation of the deposited bacterium.

In one preferred embodiment a bacterium of the invention is able to produce urease, particularly produce and secrete urease. Accordingly, in an embodiment of the invention, the bacterium is a modified strain of a bacterium as deposited at the NCIMB under accession number 42596, 42597, 42598, 42599, 42600 which has been genetically engineered to express a urease enzyme. Thus a bacterium of the deposited strains may be modified by the introduction of a nucleic acid molecule encoding a urease enzyme, such that the modified bacterium is capable of producing and secreting a urease enzyme. Nucleotide sequences encoding urease enzymes are known and widely available in the art.

As mentioned above, the methods of the present invention rely on a process of enzymatically-catalysed dissolution and re-precipitation of $CaCO_3$ to achieve cementation; $CaCO_3$ dissolved by the enzymatically-produced acid (i.e. in the pH decrease step) and subsequently allowed to re-precipitate by increasing pH is able to act as a cement, or binder, to cement, or bind, together particulate material with which it is in contact. In this way, the re-precipitated $CaCO_3$ forms the binder (cement) which together with the particulate starting material forms the construction material. The construction material can accordingly be seen as a hardened cement in the particulate material (e.g. the particulate starting material in the method above). This is achieved not only by precipitation of a new mineral phase (i.e. new grains or particles of $CaCO_3$) from the dissolved $CaCO_3$, or by the transformation of naturally reactive materials, but also by the dissolution and re-crystallization of the surface of the $CaCO_3$ grains. Thus, the grain surfaces of the $CaCO_3$ are dissolved and the dissolved $CaCO_3$ is allowed to re-precipitate (re-crystallize), including on the grain surface. This process activates the surface of the $CaCO_3$ (i.e. the grain surface), such that it is able to function as a binder, or cement. Further, precipitated crystals or particles of $CaCO_3$ may form between the particles of the particulate starting material and may act as a cement to bind the particulate starting material and the $CaCO_3$ together. The precipitation may accordingly be alternatively defined as, or as including, recrystallization of $CaCO_3$.

It will be understood from the above that a complete dissolution of the $CaCO_3$ is not required. There may be a localised dissolution and re-precipitation of the $CaCO_3$, and more particularly a localised dissolution and re-precipitation of the surface of the $CaCO_3$ (or more particularly, of the surface of $CaCO_3$ grains or particles). A part of an individual $CaCO_3$ particle or grain may be dissolved. In step (iii) of the method of forming the construction material, the binding together of the particulate starting material and precipitated $CaCO_3$ may be defined as a step of consolidation, that is the $CaCO_3$ (and specifically the precipitated $CaCO_3$) are consolidated together to form a composite material. The composite material is the construction material.

By using enzymatic reactions to cause (or induce) the changes in pH the processes of dissolution and precipitation may be controlled. Thus, enzymatic processes may be used to generate (i.e. to cause, or result in) changes in pH which may be controlled in time, or locally. In particular where microorganisms are used, microbial metabolic activity (i.e. involving the enzymes) may serve to generate the required changes in pH in a controlled manner. The microorganism, contacted with the $CaCO_3$ in the $CaCO_3$-containing preparation and provided with nutrients for growth and as a substrate for generation of acid (e.g. a sugar, such as glucose, from which a carboxylic acid can be produced) will grow and utilise the substrate to generate acid. This will reduce the pH and dissolve the $CaCO_3$ (step (i)). In particular the $CaCO_3$ may be dissolved locally, e.g. the surface of the $CaCO_3$ may be dissolved, in the vicinity of the microorganism producing the acid. When the substrate has been consumed or depleted, acid production will stop, or at least be markedly or significantly reduced, and other enzymatic reactions carried out by microorganisms (which may be the same or different to the acid-producing microorganism), e.g. hydrolysis of urea by urease, or another ammonia-generating reaction, or an acid-consuming reaction, cause an increase in pH to occur, causing the dissolved $CaCO_3$ to precipitate (step (iii)). A similar effect may be achieved using a microbial extract which contains the enzymes required for the enzymatic steps (e.g. a cell-free extract), or indeed a preparation comprising the enzymes and other reagents necessary for the enzymatic reactions. The use of a microorganism comprising enzymes for both steps (i) and (ii) advantageously means that the method may be carried out in a single step, providing all the reagents and starting materials together. Thus, the microorganism(s), $CaCO_3$, starting particulate material, nutrients and substrates for the enzymatic reactions may be provided together in the $CaCO_3$-containing preparation. However, as will be described below, this is not necessary, and for example the $CaCO_3$ may be dissolved in a first step, and the DCCP produced in this step may subsequently be contacted with the reagents of steps (ii) and (iii), together (i.e. simultaneously), or sequentially. Optionally, there may be an intervening step of removing undissolved $CaCO_3$ (i.e. the undissolved $CaCO_3$ may be removed after step (i)).

By the term “construction material” as used herein is meant a composite material formed from cement and a particulate starting material as defined below (e.g. an aggregate). The cement is formed of precipitated $CaCO_3$ crystals, which upon precipitation from solution bind the particles of the particulate starting material together to form a hardened material. The construction material is thus the consolidated product of the method. The construction material may be, or may be like, mortar or concrete. The construction material may thus be used, for instance, in masonry, to bind together stones or bricks or suchlike. Alternatively, the construction material may be used in (or may be produced as) concrete-like masonry units, blocks, bricks, slabs etc. In certain embodiments, the construction material may be used in ground stabilisation or in fundaments. For instance, the construction material may be used in the foundations of a building or suchlike. The construction material may be used for any purpose for which a cement-containing composite material is commonly used. It will be seen, therefore, that the construction material may be a solid product, or component, and may be provided in unit form (in the sense of a unit being an individual item of a masonry or construction component), e.g. a brick, block, panel, tile, column, pillar, counter-top, pre-cast veneer or any pre-cast element used in building or manufacture etc. It can thus be any shaped solid construction component. Methods of shaping or forming construction material into such a solid or shaped form are well known in the art, and any of these could be used, for example forming the construction material in a mould, compression, drying etc.

A cement is a preparation which may be used to bind materials together, including notably particulate starting materials to prepare construction materials. Cement may be used to prepare a concrete-like material. However, it may also be used to bind together already-prepared construction materials (e.g. in unit form, such as blocks or bricks). In one embodiment cement may be used to prepare a mortar to bind construction materials together.

The particulate starting material used will determine many of the properties of the construction material, and thus may be chosen based on the desired properties of the construction material. For instance, the use of an aggregate consisting of a fine material, such as sand, may yield a construction material with properties similar to mortar or low-strength concrete; use of a coarser aggregate, such as gravel, may yield a construction material with properties similar to a stronger concrete. If necessary, the construction material may be reinforced, for instance using rebar or other reinforcements such as natural (e.g. cellulose) or synthetic fibres (e.g. glass fibres, rock wool, synthetic polymer fibres, etc.).

Thus, depending on the desired characteristics of the construction material, any suitable particulate material may be used as the particulate starting material, and in particular any aggregate material (namely an aggregate material used in the construction industry, for instance soil, sand, sawdust, asphalt, a rock aggregate such as crushed stone, gravel or slag, or sintered clay or shale). The material may be natural or synthetic. Recycled materials may be used, e.g. recycled building materials, including e.g. recycled concrete. If the particulate material is crushed stone, the type of stone used is not particularly limited, so long as it does not dissolve, or substantially dissolve in the acid used to form the DCCP. Thus a $CaCO_3$-based stone, such as limestone, is not used as the particulate starting material, although it is not precluded that it may be included in the method (for example where a DCCP is prepared in a first step and added to a particulate material in step (ii), $CaCO_3$, e.g. a $CaCO_3$-based stone, or similar may be added to or included with the particulate material). In one preferred embodiment of the invention, the particulate starting material is sand, in which case any size or type of sand may be used.

When soil, sand or any other material which forms a constituent of the ground is used as the particulate starting material, the soil, sand or suchlike may be removed from the ground or may remain in the ground. In other words, in certain embodiments, the construction material may be formed within the ground, for the purpose of stabilising it. In this embodiment, the DCCP of the method, comprising the enzymes (e.g. microorganism(s)) and reagents necessary for step (iii) of the method is effectively poured into the ground wherein the resultant cement binds together loose particulates, consolidating and thus stabilising the ground.

The size of the particulate material is not critical and may be varied within wide limits, according to choice, for example depending on the nature of the desired construction material. In some embodiments large particles may be used, e.g. aggregates comprising particles of cm or mm size, e.g. gravels, stones, crushed rocks etc. Thus the size range of particles may in a representative range be from 1 μm, or 10 μm, to 5 cm, or more. In some embodiments the particulate starting material may consist of, or at least essentially consist of, small particles, in particular particles on a μm scale. In other words, the particles may be between, or in the range of 1 μm and 1 mm (1000 μm) in size, for instance between, or in the range of, 100 and 1000 μm or 100 and 500 μm, for example 200 and 400 μm, or 200 and 300 μm. Sand may for example comprise particles in this size range. Any commercially-available sand product may be used, for example sand typically used in cement manufacture. Large size particles may however be, for instance, between 1 mm and 2 mm in size, or have a wider range in size, for instance between 100 μm and 2 mm. By size here is meant the length of the longest dimension of the particle; if the particle is a sphere, its size is its diameter.

The $CaCO_3$ which is used in the method of the invention may be provided in any form. Thus, it may be any rock or stone comprising or based on $CaCO_3$. For instance, it may be in any crystal or polymorphic form: calcite, aragonite or vaterite. The $CaCO_3$ may be obtained from any suitable source rock, i.e. a rock which is predominantly formed from, or at least contains, $CaCO_3$. In particular, it may be any carbonate rock composed predominantly of calcite or aragonite (this includes rocks where $CaCO_3$ is the main ingredient. Useful source rocks of the invention include marble and various forms of limestone, such as tufa and travertine, and chalk. Chalk may be viewed as a type of limestone, typically as a soft and white form of limestone, composed of the calcite form of $CaCO_3$, but geologically speaking it is a distinct type of carbonate rock, specifically a sedimentary calcium-bearing rock. In engineering terms, the term chalk is also used to refer to a crushed limestone. Preferably, the $CaCO_3$ used in the method is in the form of limestone or chalk. A $CaCO_3$-containing preparation is any preparation or composition containing the $CaCO_3$, i.e. containing a $CaCO_3$ material. Thus, it may be a suspension of the $CaCO_3$ in a medium, generally an aqueous medium, suitable for carrying out the enzymatic steps (i) and (iii). The preparation may contain one or more of the other reagents and components for carrying out the method.

When $CaCO_3$ is dissolved in acid, the dissolution occurs at the surface of the $CaCO_3$, where the $CaCO_3$ is in contact with the acid. The rate of dissolution of $CaCO_3$ will therefore be increased if the surface area of the $CaCO_3$ exposed to the acid is increased, particularly if the ratio of the surface area of the $CaCO_3$ to its volume is increased. The $CaCO_3$ dissolved in acid may therefore be in the form of a particulate material, including in particular a powder. A $CaCO_3$ powder may be obtained by for instance crushing and/or grinding $CaCO_3$ or a $CaCO_3$-containing rock.

Preferably the $CaCO_3$ powder consists of, or at least essentially consists of, particles no more than 1 mm and no less than 1 μm in size. In other words, the particles may be between, or in the range of, 1 μm and 1 mm in size, for instance between, or in the range of, 1 μm and 900 μm, 1 μm and 800 μm, 1 μm and 700 μm, 1 μm and 600 μm, 1 μm and 500 μm, 1 μm and 400 μm, 1 μm and 300 μm, 1 μm and 200 μm or 1 μm and 100 μm. As for the particulate material described above, by size here is meant the length of the longest dimension of the particle.

By enzymatically generating an acid in a $CaCO_3$-containing preparation, the pH of the preparation is decreased, dissolving the $CaCO_3$. As noted above, by $CaCO_3$-containing preparation is meant a material which comprises $CaCO_3$ (as described above) and may further comprise other substances. For instance, the $CaCO_3$-containing preparation may comprise the particulate starting material, and/or one or more of the reagents for enzymatically increasing the pH of the material in step (iii) of the method, e.g. urea.

The acid used to dissolve $CaCO_3$ in the method of the invention is generated enzymatically. That is to say, a non-acid substrate is converted into the acid using enzymes. Suitable substrates are discussed further below. The identity of the acid is otherwise not particularly limited, provided that it is suitable for use with the particulate starting material (i.e. it will not dissolve or chemically react with the particulate starting material) and will not denature the enzyme(s) used to generate an increase in pH later in the method.

Preferably, the enzymatically generated acid is a carboxylic acid. The carboxylic acid may be a monocarboxylic acid (with one carboxyl group), a dicarboxylic acid (with two carboxyl groups), a tricarboxylic acid (with three carboxyl groups) or a polycarboxylic acid (with more than three carboxyl groups), provided it is generated enzymatically. Similarly, a straight-chain or branched-chain carboxylic acid may be used, as may a cyclic or aromatic carboxylic acid, provided it is generated enzymatically. Carboxylic acids may conveniently be enzymatically generated by a process of fermentation. Preferred carboxylic acids which may be enzymatically generated in the method of the invention include acetic acid, formic acid, propionic acid, butyric acid, gluconic acid, succinic acid and lactic acid. For example, lactic acid may be produced by fermentation of glucose, a process whereby glucose is firstly converted to pyruvate by glycolysis, and the pyruvate is then converted to lactic acid by lactate dehydrogenase. The skilled individual will be aware of many other carboxylic acids that may be enzymatically produced, and how these other carboxylic acids may be enzymatically produced. Combinations of acids may be used, for example lactic acid and acetic acid. In particular, where a microorganism is used more than one acid may be produced by the organism. In some embodiments the microorganism may be selected or engineered to produce only one, or predominantly only one, carboxylic acid, for example lactic acid. Isolates have been obtained which produce only lactic acid.

The enzymatic generation of an acid may be performed using a microorganism, or using a microbial extract which contains enzymes (an enzyme-containing microbial extract). When a microorganism is used to perform the enzymatic generation of the acid, the microorganism is present or included in the $CaCO_3$-containing preparation or is added to it to initiate acid generation. Nutrients for use by the microorganism (i.e. which it can use for growth, e.g. carbon source, nitrogen source, amino acids, nucleotides etc.) may also be included in the preparation. The nutrients may be included in the preparation in the form of a growth or culture medium. Such media include e.g. LB medium, TY medium etc., though a defined medium may be preferable such that the metabolism of the microorganism can be more closely controlled. As described in more detail below, a substrate is required for the enzymatic reactions, including for the production of acid. A carbon source, e.g. a sugar such as glucose, provided for growth may also serve as substrate for acid generation, or separate carbon sources and substrates may be added.

Thus, supplements for use by the microorganisms as substrates for acid production may also be included in or added to the $CaCO_3$-containing mixture. The substrate for acid production may also be a nutrient. In particular, the substrate may be a sugar. Any suitable sugar (i.e. any sugar that can be enzymatically converted into an acid (particularly a carboxylic acid, preferably lactic acid or acetic acid)) may be used. Preferably a six-carbon sugar (i.e. a hexose) is used, such as glucose, galactose or fructose. A disaccharide of six-carbon sugars, such as sucrose or lactose, may also be a suitable substrate, provided that the microorganism performing the conversion of the substrate into acid is able to hydrolyse the disaccharide into its constituent monosaccharides. In one preferred embodiment the substrate for acid production is the monosaccharide glucose.

However, any convenient or desirable carbohydrate or carbohydrate source may be used as the substrate, particularly any source of readily metabolizable, or utilisable, sugars, and this may depend on the enzymes/microorganisms used. Suitable carbohydrates, preferably easy utilizable sugars, may be derived from hydrolysis (e.g. enzymatic hydrolysis) of biomass or other waste or recycled materials, for example cellulose or cellulosic materials (such as from e.g. lignocellulosic biomass). Such materials may be available as sidestreams from agriculture and forestry.

It is also included that microorganisms used in the methods of the invention perform such hydrolysis steps themselves and produce acid from the resulting sugars. Thus, the substrate for acid production may be a direct substrate (such as a sugar) or it may be an indirect substrate, which may itself be metabolised, or enzymatically converted, into a substrate for acid production.

When a microorganism is used to perform the enzymatic generation of acid, the microorganism produces enzymes which catalyse a metabolic pathway whereby the substrate is converted into acid. When a microorganism is used to perform the enzymatic generation of acid, this step (i.e. the generation of acid) may preferably be performed under aerobic conditions. As will be known to the skilled individual, many microorganisms produce carboxylic acids as end products of anaerobic metabolism. It falls under the scope of the invention that the enzymatic production of acid takes place using a microorganism under anaerobic conditions (in which case either a facultative anaerobe or an obligate anaerobe may be used in the process). However, as mentioned above, it is a preferred embodiment of the invention that the enzymatic generation of acid is performed using a microorganism under aerobic conditions. The microorganism used to generate acid under aerobic conditions may be an obligate aerobe or a facultative anaerobe, so long as it produces acid under aerobic conditions.

By aerobic conditions, according to the invention, is meant conditions in which oxygen is present at a level sufficient that a facultative anaerobe (i.e. an organism able to grow both in the presence and absence of molecular oxygen ($O_2$)) can perform aerobic respiration. For instance, aerobic conditions may be normal atmospheric conditions, i.e. conditions in which the reaction atmosphere contains approximately the same proportion of oxygen as is found in the earth's atmosphere, i.e. approximately 21% v/v. Normal atmospheric conditions may contain from 15 to 25% oxygen, such as from 18 to 24% or from 20 to 22% oxygen. When the bacterium is cultured in liquid medium under aerobic conditions, the liquid may contain approximately as much dissolved oxygen as an aqueous solution exposed to normal atmospheric conditions (e.g. 1-10 mg/L dissolved oxygen). However, conditions may be considered aerobic even if the amount of dissolved oxygen is less than this, so long as it meets the requirement detailed above (i.e. that sufficient dissolved oxygen is present that a facultative anaerobe can perform aerobic respiration).

The enzymatic generation of the acid may alternatively be performed using an enzyme-containing microbial extract. In this embodiment, a microbial culture is grown, the constituent microbes of which express the enzymes which perform the catalytic steps of a metabolic pathway whereby the substrate is converted into acid. From such a culture an enzyme-containing microbial extract may be obtained. Once a certain level of growth is reached, the microorganisms in the microbial culture are isolated from the medium, e.g. by centrifugation, and lysed (e.g. by sonication or high pressure homogenization, though a skilled individual will be aware of various other methods by which a cell extract can be obtained). The lysate obtained is an enzyme-containing microbial extract, which may be applied to the $CaCO_3$-containing preparation. In this embodiment, a substrate for acid generation (as described above) will also need to be added to or included in the $CaCO_3$-containing preparation, which the enzymes in the enzyme-containing microbial extract can convert to acid, but no other nutrients would of course be required. It is more preferable that a microorganism is used to perform the enzymatic generation of acid than that an enzyme-containing microbial extract is used.

The microorganism used to perform the enzymatic generation of acid, or the microorganism from which the enzyme-containing microbial extract is derived, may be a prokaryote, such as a bacterium (by which is meant a eubacterium) or an archaeon, or it may be a eukaryote, such as a fungus, particularly a yeast. Preferably though, the microorganism is a bacterium, most preferably a lactic acid-producing bacterium or an acetic acid-producing bacterium. Such a bacterium may be Gram-positive or Gram-negative.

An individual skilled in the art will be readily able to identify whether a microorganism produces acid. For instance, acid production by a microorganism can be identified by growth of the microorganism on RM-9.5 medium agar (see Examples) at an alkaline pH. Acid-producing microorganisms will alter the colour of the alkaline medium from blue to yellow. The identity of the acid produced can then be identified by e.g. HPLC.

When a microorganism is used to perform the enzymatic generation of acid, the microorganism must be able to produce high levels of acid (preferably lactic acid or acetic acid), in order to dissolve $CaCO_3$; they must be able to grow under conditions of high pH and high ionic strength, reflecting the conditions associated with high levels of dissolved limestone. Preferably, the microorganism can also grow and produce acid under conditions of low oxygen availability, and/or are able to sporulate (for ease of handling). Most preferably, the microorganism is able to produce a carboxylic acid (preferably lactic acid or acetic acid) to a concentration of at least 30 mM, in order to dissolve $CaCO_3$. Microorganisms able to produce even higher carboxylic acid concentrations are preferred. The concentration of acid produced can be calculated from quantifying analysis by e.g. HPLC.

The inventors of this application were unable to identify any commercially-available species or strains of microorganism having all of the above characteristics, and therefore suitable for use in this aspect of the invention. However, the inventors were able to isolate novel, previously unknown bacterial strains from sites close to a limestone quarry in central Norway, which met the above-described requirements. A large number of such isolates were obtained. Accordingly, the inventors have shown that when an appropriate site or source of microorganisms is selected, that is a site where $CaCO_3$ is present, suitable microorganisms, particularly bacteria, may be isolated, which are suitable for use in the methods of the invention. These strains are believed to be of previously unknown species, but are all related to species of the genus *Bacillus*. Representative strains have been deposited at the NCIMB with accession numbers as indicated above. In preferred embodiments of the invention, one or more of these strains is used to perform the enzymatic generation of acid, preferably lactic acid and/or acetic acid, by fermentation of a sugar, preferably glucose. Alternatively, an enzyme-containing microbial extract may be derived from one of these strains and used to perform the enzymatic generation of acid.

The enzymatically generated acid dissolves at least part of the $CaCO_3$ in the $CaCO_3$-containing preparation. That is to say, at least some of the $CaCO_3$ in the preparation is dissolved. It may be that all of the $CaCO_3$ is dissolved in the acid, though this is not necessary, so long as sufficient $CaCO_3$ is dissolved that the $Ca^{2+}$ concentration in the resultant dissolved calcium carbonate preparation (DCCP) is high enough that sufficient $CaCO_3$ may be eventually precipitated out of the DCCP to bind together the aggregate (the particulate starting material). In particular, where chalk particles are used as the $CaCO_3$-containing material, the particles may be only partially dissolved, leaving small chalk particles in the DCCP. Although this is not a necessary requirement, the DCCP may in one embodiment be a $Ca^{2+}$-saturated solution, which as herein defined requires that at least 15 g of $CaCO_3$ be dissolved per litre of acid. In such an embodiment sufficient substrate is added to or included in the $CaCO_3$-containing preparation that the acid is produced to a sufficient concentration or in a sufficient amount to dissolve at least 15 g $CaCO_3$ per litre of acid. Such an amount of substrate may be readily identified by trial and error. However, as indicated above, such a high concentration of $Ca^{2+}$ ions is not necessary to perform the method of the invention and lower concentrations may be used (thus the amount of acid produced may be less than that required to produce a saturated solution). The amount of acid produced is not critical, as long as it sufficient to dissolve at least part of the $CaCO_3$ in the $CaCO_3$-containing preparation, to allow cementation to occur. For example the concentration of acid in the DCCP may be much lower, e.g. about 0.02 to 0.05 M.

The DCCP that is obtained is then combined with the particulate starting material. The particulate starting material may be present in the $CaCO_3$-containing preparation prior to the enzymatic generation of acid. In this instance, the DCCP and the particulate starting material are combined simply by the production of the DCCP by the dissolution of $CaCO_3$ in the acid, i.e. the combining process is passive and does not require an active step of combining performed by an individual. Alternatively, the particulate starting material may not be present in the $CaCO_3$-containing preparation prior to the generation of acid therein, in which case the DCCP and the particulate starting material must be actively combined following DCCP formation.

The DCCP/particulate starting material mixture is then hardened (or consolidated) by causing the dissolved $CaCO_3$ in the mixture to precipitate, yielding $CaCO_3$ crystals that bind together the particulate starting material to form a composite construction material. The $CaCO_3$ in the mixture is caused to precipitate by an increase in the pH of the mixture. This increase in the pH of the mixture is enzymatically generated.

Like the enzymatic generation of acid earlier in the method, this enzymatic generation of an increase in pH may be performed using a microorganism or an enzyme-containing microbial extract. Any reagent(s) may be used in this pH-increase step, so long as they may be used as substrate(s) for an enzyme-catalysed reaction which results in a pH increase. In a preferred embodiment of the invention, urea is hydrolysed by urease, which produces ammonium and thus drives an increase in pH. Alternatively, other ammonia-generating enzymatic reactions may be employed, or other reactions which result in a pH increase, such as for example reactions which utilise acid as a substrate. It is commonly known that many microorganisms utilize carboxylic acids as carbon source, including strains that are acid producers, and once the substrate for acid production (e.g. the sugar) is depleted, the microorganism continues using the produced acid as alternative C source.

All reagents used for this step of increasing the pH of the mixture may be present in the $CaCO_3$ preparation prior to step (i). For instance, where urea hydrolysis is used to increase the pH of the mixture, the urea may be present in the $CaCO_3$-containing preparation prior to the initiation of acid generation.

Alternatively, the reagents for step (iii) (e.g. urea) may only be added after step (i) has been performed. In other words, the DCCP is formed first, combined with the particulate starting material and then the reagents for step (iii) are added. In this instance, the reagents for step (iii) may be added before, during or after step (ii), in other words at any point after the DCCP is formed. In certain embodiments, when the reagents for step (iii) are not present in the $CaCO_3$-containing preparation during step (i), if the particulate starting material is also not present in the $CaCO_3$-containing during step (i), undissolved $CaCO_3$ can be removed from the DCCP by e.g. filtration, prior to the combination of the DCCP with the particulate starting material and the reagents of step (iii). However, in certain preferred embodiments of the invention, undissolved $CaCO_3$ is not removed from the DCCP, and instead acts as part of the aggregate which is bound together by the $CaCO_3$ cement, when the $CaCO_3$ precipitates in step (iii) and thus hardens the material. This is inherently the case when the $CaCO_3$-containing preparation comprises the particulate starting material and/or the reagents for step (iii) prior to and/or during the production of the DCCP.

As described above, the enzymatic generation of an increase in pH may be performed using a microorganism or an enzyme-containing microbial extract, as may be the enzymatic generation of an acid which causes a pH decrease in step (i). However, it may be that neither of these steps is performed using a microorganism or an enzyme-containing microbial extract, instead being performed using (an) isolated and purified or commercially acquired enzyme(s). For instance, if the enzyme-generated increase in pH is caused by hydrolysis of urea by urease, this hydrolysis may be performed using e.g. commercially acquired Jack bean (*Canavalia ensiformis*) urease (Sigma-Aldrich U7752). However, preferably at least one of the enzymatic generation of an acid which causes a pH decrease in step (i) and the enzymatic generation of an increase in pH in step (iii) is performed using a microorganism or an enzyme-containing microbial extract, and most preferably both of these enzyme-mediated steps are performed using a microorganism or an enzyme-containing microbial extract. The enzymatic generation of an acid which causes a pH decrease in step (i) and the enzymatic generation of an increase in pH in step (iii) may both be performed using a bacterium or an enzyme-containing bacterial extract.

Thus, in a preferred embodiment of the invention, the enzyme-generated increase in pH of step (iii) is performed using a microorganism (preferably a bacterium) which produces urease, or an enzyme-containing microbial extract (preferably an enzyme-containing bacterial extract) which is derived from a urease-producing bacterium, and which therefore contains urease, to hydrolyse urea, thus increasing the pH of the mixture.

It will be straightforward for the skilled person to determine whether a microorganism produces urease. For instance, microorganisms which produce urease can be identified by growing strains on Christensen urea medium agar at neutral pH (see Examples). Strains which produce urea will cause the medium to change colour from yellow to red.

In a particularly preferred embodiment of the invention, the generation of acid which causes the pH decrease in step (i) and the enzyme-generated pH increase in step (iii) are both performed using the same microorganism. In such an embodiment, the microorganism first produces a carboxylic acid by e.g. fermentation of a sugar, reducing the pH of the mixture and dissolving at least part of the $CaCO_3$ in the $CaCO_3$-preparation. Then, when the sugar has been used up (i.e. all or substantially all of the sugar has been converted to acid), the microorganism will start to produce urease, which hydrolyses urea, forming ammonium and thus increasing the pH of the solution.

In one embodiment the urea may be present in the $CaCO_3$-containing preparation in step (i) of the method. In certain such embodiments urease production by a microorganism may be controlled, e.g. induced. For example it may be induced upon sugar depletion, or upon generation of sufficient acid. Alternatively, the urea may not be present in the $CaCO_3$-containing preparation in step (i) of the method. In this case, the urea may be added to the DCCP after it has been formed. In such a case, the addition of urea to the microorganism-containing DCCP may stimulate the microorganisms to produce urease. It is not necessary for all the substrate for acid production to be consumed, as long a sufficient acid is generated to dissolve sufficient $CaCO_3$ for cementation to occur.

As previously described, no commercially-available microbial strain was identified by the inventors as suitable for use in the enzymatic generation of acid to dissolve $CaCO_3$ in step (i) of this invention, but it was found possible to isolate suitable strains from a limestone-containing environment. Five such representative suitable strains, isolated from sites close to a limestone quarry in Norway, have been deposited at the NCIMB. Of these strains, one (UP-009, closely related to *Bacillus weihenstephanensis*) was also able to produce urease.

Thus, in a preferred embodiment, the bacterium of strain UP-009, with the NCIMB accession number 42600, is used both to generate acid to dissolve the $CaCO_3$ in the $CaCO_3$-containing preparation of step (i), and to generate an increase in the pH of the mixture in step (iii) by the use of urease to hydrolyse urea. Alternatively, one of the other deposited lactic acid-producing strains of bacteria (as defined above) may be engineered to produce urease, such that the strain can be used both in the production of lactic acid and for the production of urease. Methods for the engineering of bacterial species to produce exogenous proteins, including the introduction of metabolic pathways (i.e. genes encoding enzymes to perform one or more reactions in concert) are well known in the art of microbiology. Further, commercial urease-producing strains may also be used, e.g. *Sporosarcina pasteurii* DSM33, and as further described below.

In other embodiments, microorganisms (preferably bacteria) or enzyme-containing microbial extracts (preferably enzyme-containing bacterial extracts) are used both to generate the acid which causes the pH decrease in step (i) and to perform the enzyme-generated pH increase in step (iii), but different microorganisms/enzyme-containing microbial extracts are used for each purpose. In other words, a first microorganism or enzyme-containing microbial extract is used to generate the acid which decreases the pH in step (i) of the method, and a second microorganism or enzyme-containing microbial extract is used to perform the enzymatic generation of an increase in pH in step (iii). When the enzymatic generation of an increase in pH in step (iii) is achieved by hydrolysis of urea by urease, the second microorganism may be any urease-producing microorganism. Its identity is not, therefore, particularly limited. Suitable species of microorganism can be found, for instance, in U.S. Pat. Nos. 8,182,604, 8,728,365 and 8,951,786, and include e.g. *Sporosarcina pasteurii, Sporosarcina ureae, Proteus vulgaris, Bacillus sphaericus, Myxococcus xanthus, Proteus mirabilis* and *Helicobacter pylori*. Alternatively, the microorganism may be a strain which does not natively produce urease but has been engineered to do so. It will be straightforward for the skilled individual to engineer a microorganism to render it urease-producing.

In certain embodiments of the method, the pH increase of step (iii) is not generated by the enzymatic processing of an additional reagent. Rather, the pH increase of step (iii) is generated by the metabolic removal of acid by a microorganism. In other words a microorganism, which may or may not be the same microorganism as was used to generate the acid in step (i), metabolises the acid and thus removes it from the mixture, causing the pH of the mixture to increase. As indicated above, it is known that microorganisms may degrade acids that they have themselves produced.

The steps of the method may be conducted in any convenient way, depending for example on the nature of the construction material it is intended to produce. Thus the various ingredients (reaction components) may simply be contacted (e.g. added together) and allowed to react. Thus, microorganism(s), $CaCO_3$, starting particulate material, nutrients and substrates for one or both of the enzymatic reactions may be provided together, optionally mixed, and the reactions of dissolution and precipitation of the $CaCO_3$ may be allowed to occur, e.g. without any (further) mixing. Alternatively, the reaction mixture may be mixed during the dissolution step (step (i)), but without mixing during precipitation and consolidation (step (iii)). The reactions may also be performed in a wide temperature range; including at room or ambient temperature, including outdoor temperatures, for example at construction sites. Heating of the reaction mixture(s) is not required, and "incubation" of the microorganisms may simply take place by standing, or holding, of the reaction mixtures for a period of time. Thus, for example, a temperature range of 10 to 40° C. may be used, or possibly even lower temperatures.

The step of generating an increase in the pH of the mixture in step (iii), thereby causing $CaCO_3$ to precipitate and to bind together the particulate material (i.e. to consolidate), may be performed in a mould, thus allowing the size and shape of the resultant construction material to be determined. In some embodiments, depending on when the materials in the mixture are combined (as described above), the entirety of the method (i.e. steps (i), (ii) and (iii)) may be performed in the mould. The consolidation, or hardening, of the construction material may be performed over a period of several hours, e.g. at least 5 hours, at least 10 hours, at least 20 hours, at least 50 hours or at least 100 hours. Optimal timespans for the method may be determined by the skilled person.

The relative amounts of $CaCO_3$, particulate starting material and, where relevant, urea used in the method may be varied considerably. As described above, in one embodiment the DCCP may be a saturated $Ca^{2+}$ solution, containing at least 15 g/L $CaCO_3$, preferably at least 20, 25 or 30 g/L $CaCO_3$. However, in other embodiments the DCCP may contain lower concentrations, or amounts, of $CaCO_3$. In some representative embodiments, the particulate starting material may be combined with the DCCP at a concentration of between, or in the range of, 1.5 kg/L and 4 kg/L, preferably between, or in the range of, 2 kg/L and 3 kg/L, and urea may be combined with the DCCP (e.g. included or added to the $CaCO_3$-containing preparation) to give a resultant concentration preferably between, or in the range of, 50 mM and 500 mM, most preferably between, or in the range of, 100 mM and 200 mM. In other embodiments, lower concentrations may be used.

In order to aid or improve the hardening of the above-described mixture into a composite material, it may be advantageous for the mixture to be compacted prior to initiation of the hardening (consolidation) (precipitation and binding). For instance, the $CaCO_3$-containing preparation, and any other reagents pre-mixed with it prior to step (i), may be compacted in a mould prior to its combination with the DCCP. Following hardening, it may also be advantageous to wash by-products and suchlike out of the construction material using water, and/or to dry the material by heating, e.g. in an oven, for between, or in the range of, e.g. 1 and 5 hours at a temperature e.g. between, or in the range of, 50 and 80° C.

The invention also provides a construction material formed by the method of the invention, as described above. Such a material consists of aggregate particles, e.g. sand or stone such as gravel, bound together by precipitated $CaCO_3$ crystals. It is these crystals which form the cement. As described above, the construction material may also comprise particles of undissolved $CaCO_3$ (e.g. limestone or chalk), which when present is also bound together by precipitated $CaCO_3$ crystals. The construction material will also comprise within it the anions of the acid used to dissolve $CaCO_3$ in the first step of the method. When a carboxylic acid is used for this purpose, the anions are the organic carboxylate ions, e.g. if lactic acid is used lactate molecules will be present in the construction material.

The invention further provides a method of forming a cement from $CaCO_3$, said method comprising:

(i) enzymatically generating an acid in a $CaCO_3$-containing preparation to decrease the pH of said preparation, thereby dissolving at least a part of the $CaCO_3$ to produce a dissolved calcium carbonate preparation (DCCP);

(ii) optionally combining the DCCP with a particulate material; and (iii) enzymatically generating an increase in the pH of said DCCP or said combined mixture of (ii) thereby causing at least a part of the dissolved $CaCO_3$ to precipitate to form a cement, wherein the precipitated $CaCO_3$ is able to function as a cement to bind together particulate or other construction materials;

wherein where the method comprises step (ii) the $CaCO_3$ and the particulate material may be separate or pre-mixed prior to (i), such that in step (ii) the combination of the DCCP with the particulate material may take place simultaneously with or after the production of the DCCP, and wherein one or more of the reagents for enzymatically increasing the pH in step (iii) may be present in the $CaCO_3$-containing preparation, or may be added during or after any one of steps (i) or (ii), or in step (iii).

In this method, the enzymatic generation of an acid, the acid, the $CaCO_3$-containing preparation, the particulate starting material, the DCCP and the enzymatic generation of an increase in pH are all as defined above.

The $CaCO_3$ cement may be used to bind together construction materials, particularly masonry units such as bricks, slabs, blocks, concrete units etc. The DCCP may be combined with a particulate material, preferably sand, to yield a mortar or mortar-like material which may be used to bind together construction materials. Alternatively, the $CaCO_3$ cement may be used alone to bind together the construction materials, i.e. without containing a particulate starting material or aggregate. By "bind together" is meant that the bound construction materials are stuck together and cannot be easily separated, such as when bricks are bound together by mortar in bricklaying. In particularly preferred embodiments, the construction materials are made using the method of the first aspect of the invention (i.e. they consist of a construction material of the invention).

In a further aspect, the invention provides a method of connecting construction materials together, said method comprising applying a cement prepared according to the paragraphs immediately above to at least one construction material unit and placing it together with at least one other construction material unit. In this embodiment the cement effectively functions as a mortar. The construction material units may be bricks, slabs, blocks, etc. Most preferably, the construction material units consist of a construction material made according to the method of the first aspect of the invention (i.e. the construction material units consist of a construction material of the invention).

The method of connecting construction materials together may be used in any form of construction. For instance, it may be used in bricklaying, paving, roofing, road building, etc. When construction materials are connected according to this aspect of the invention, they are bound together as described above.

The invention further provides a bacterium suitable for use in the methods of the invention, particularly in the production of acid in the methods of the invention, said bacterium being:

(i) alkaliphilic;

(ii) able to produce acid under aerobic conditions at a pH of at least 8.5 (particularly in the presence of $CaCO_3$, e.g. limestone, and more particularly also under low oxygen conditions); and (iii) able to dissolve $CaCO_3$ to produce $Ca^{2+}$ ions, (particularly in the presence of glucose and $CaCO_3$ powder)

In particular the bacterium may be a bacterium (i.e. a species or strain) of the genus *Bacillus* or *Jeotgalibacillus*, or any other *Bacillus*-related species, as long as it has the properties indicated above.

The ability to produce acid and to dissolve $CaCO_3$ to produce $Ca^{2+}$ ions may be determined as described further below. In particular, the bacterium may be able to dissolve $CaCO_3$ to produce $Ca^{2+}$ ions at a temperature range of e.g. 10 to 40° C. or 10 to 35° C., more particularly 15 to 30° C., or more generally at a temperature below 30° C., or at around 20° C. Further, the bacterium may be able to dissolve $CaCO_3$ to produce $Ca^{2+}$ ions when provided with glucose and $CaCO_3$ and allowed to stand, without mixing. Thus, the bacteria may be able to produce acid and dissolve the $CaCO_3$ when incubated, or allowed to grow, in the presence of glucose and $CaCO_3$, but also simply when contacted with, or provided with glucose and $CaCO_3$ (i.e. without necessarily been placed under growth conditions, or without incubation with heating and/or aeration).

Preferably, the bacterium is capable of forming spores.

A spore is a metabolically inactive, dormant form of a bacterium. Such spores are easy to handle as they require no nutrients and are largely resistant to changes in temperature and atmospheric conditions. The bacterium capable of forming spores is in particular capable of forming endospores. Such bacteria particularly include members of the phylum "Firmicutes", such as *Clostridia* and *Bacilli*. Bacteria capable of forming spores may be identified by e.g. culturing the bacteria in nutrient-poor medium, heating the culture at high temperature for a period of time sufficient to kill vegetative cells (e.g. at 80° C. to 100° C. for 10 to 30 mins) and then plating the heated culture onto suitable growth medium (which may for example be a rich or a defined or minimal medium). Resultant bacterial colonies can be assumed to be of spore-forming bacteria, the colonies derived from germination of spores on the growth medium. The skilled individual will be aware of other methods of spore isolation, such as culture incubation in ethanol or suchlike to kill vegetative cells.

By alkaliphilic is meant an organism (in this case a bacterium) capable of growth under alkaline conditions. Such a bacterium is able to grow at a pH of at least 8, preferably at least 8.5 or at least 9. The bacterium is also able to produce acid at a pH of at least 8.5, preferably at least 9. In particular, the bacterium is able to produce acid in the presence of $CaCO_3$, the presence of which may cause a high pH in a mixture. The acid produced by the bacterium is preferably a carboxylic acid, such as acetic acid, formic acid, propionic acid, butyric acid, gluconic acid, succinic acid or lactic acid. Such an acid may be produced by fermentation, preferably fermentation of a sugar, particularly a hexose sugar such as glucose, fructose or galactose.

More particularly, the bacterium of the invention is able to produce acid at a pH of at least 8.5 under aerobic conditions. Aerobic conditions according to the invention are defined above. Furthermore, the skilled person will understand the term aerobic conditions in relation to bacterial culturing. Fundamentally, aerobic conditions are the opposite of anaerobic conditions. At a basic level, if, in order for a bacterium to produce acid, the amount of oxygen in the bacterial growth conditions must be reduced relative to atmospheric conditions, the bacterium can be understood as being unable to produce acid under aerobic conditions. Thus, according to the invention, a bacterium able to produce acid under aerobic conditions is able to produce acid under atmospheric conditions or under conditions whereby the amount of oxygen present has not been reduced by human intervention.

Though bacteria of the invention are able to produce acid under aerobic conditions, this does not preclude them being also able to produce acid under low oxygen conditions or anaerobic conditions also. The bacterium of the invention may thus be an obligate aerobe or a facultative anaerobe, but may not be an obligate anaerobe. The bacterium may be able to produce acid under anaerobic conditions and aerobic conditions. Preferably, the bacterium of the invention is able to produce acid under low-oxygen conditions.

By "low-oxygen conditions" is meant conditions with less oxygen than under normal growth conditions. This means not only less oxygen than under normal atmospheric conditions, but also less dissolved oxygen than would ordinarily be present in aqueous solution. However, it does not mean that there is no oxygen present, i.e. low-oxygen conditions are aerobic conditions. By anaerobic conditions is meant conditions under which no or essentially no oxygen is present. Such conditions may be identified using e.g. a redox indicator, such as resazurin. A bacterium able to grow and produce acid under anaerobic conditions may thus be identified by testing its ability to grow and produce acid under such conditions (e.g. in an anaerobic cabinet or chamber). A bacterium able to grow and produce acid under low-oxygen conditions may be identified by testing its ability to grow and produce acid under conditions of reduced oxygen, or simply in a culture which is not properly aerated (e.g. in a liquid culture grown in a container, such as a flask or bottle, which is largely full of liquid (such that minimal environmental oxygen is present), sealed and is incubated without shaking). The skilled individual will be able to identify conditions whereby a culture is not properly aerated without difficulty, e.g. by simply growing a culture without the conditions usually used to ensure proper aeration of a bacterial culture.

Alkaliphilic, acid-producing bacterial strains can be identified as follows: Strains are plated onto agar made up with RM-9.5 medium (1.0 g/L yeast extract (Oxoid), 3.0 g/L peptone (Oxoid), 10.0 g/L glucose, 5.0 g/L NaCl, 2.5 ml/L thymol blue solution (1% w/v), 15 g/L agar; pH 9.5 (the pH was adjusted to 9.5 using 1.2 g/L $Na_2CO_3$)). Strains able to grow on this medium are alkaliphilic, and acid production can be identified by a change in the colour of the medium from blue to yellow, caused by the associated decrease in pH. However, the skilled individual will be aware of other methods by which alkaliphilic, acid-producing bacteria may be identified. As described, the above test may be performed under aerobic conditions (including low-oxygen conditions) and anaerobic conditions to identify bacteria able to produce acid under the respective growth condition.

The bacterium is able to dissolve $CaCO_3$ to produce $Ca^{2+}$ ions. This dissolution of $CaCO_3$ is achieved by the acid produced by the bacterium. The bacterium is thus able to dissolve $CaCO_3$ particularly under conditions where it will produce acid, such as when a fermentable sugar (e.g. glucose) is present. The dissolution of $CaCO_3$ occurs when a mineral consisting of $CaCO_3$, or which at least comprises $CaCO_3$ at its surface, is contacted by an acid. Maximal dissolution of $CaCO_3$ can thus be achieved by maximising the $CaCO_3$ surface area which is in contact with the acid. For any given amount of $CaCO_3$ this can thus be achieved by providing it in a particulate form, e.g. a powder.

Accordingly, an assay for $CaCO_3$ dissolution may be performed as follows: $CaCO_3$ powder is mixed with RM-9.5 medium containing 30 g/L glucose and 10 g/L $CaCO_3$ to which a volume of bacterial culture has been added (for example 15 g $CaCO_3$ powder in a 50 ml reaction tube to which a mixture of 120 μl bacterial culture and 6 ml of medium containing the glucose is added). The mixture is incubated standing and covered with parafilm at room temperature and monitored for acid and $Ca^{2+}$ production using pH and $Ca^{2+}$ electrodes present in the culture vessel (e.g. 50 ml tube) over a period of time, e.g. from 6 to 24 hours, e.g. from 8, 10, 12, 14 or 16 hours to 18, 20, 21, 22 or 24 hours.

In certain embodiments of the invention, the bacterium is strain AP-004, which has the NCIMB accession number 42596, strain AP-006, which has the NCIMB accession number 42597, strain AP-029, which has the NCIMB accession number 42598, strain AP-044, which has the NCIMB accession number 42599, or strain UP-009, which has the NCIMB accession number 42600. As described above, these strains are all spore-forming, alkaliphilic, acid-producing strains, which are able to grow and produce acid under low oxygen conditions and which are able to dissolve $CaCO_3$ to produce $Ca^{2+}$ ions using the acid they produce. The bacterium may alternatively be a derivative of one of these strains, e.g. a mutant of one of these strains, or a modified variant or derivative of one of these strains, e.g. which carries one or more non-native plasmids.

In a most preferred embodiment, the bacterium is further able to produce urease. Such a bacterium may be identified, for instance, by growth on Christensen urea medium (1.0 g/L peptone, 10 g/L glucose, 5.0 g/L NaCl, 2.0 g/L $KH_2PO_4$, 20.0 g/L urea, 0.012 g/L phenol red, 15 g/L agar; pH 6.5). Bacterial production of urease causes an increase in pH which changes the colour of the medium from yellow to red. The skilled individual will be aware of other methods of detecting urease production by a bacterium. In a preferred embodiment, the bacterium is strain UP-009, which has the NCIMB accession number 42600. As described above, UP-009 is a urease-positive, acid-producing bacterium. Alternatively, the bacterium may be a derivative of UP-009, such as a mutant strain or a strain thereof carrying a plasmid. In another embodiment, the bacterium may be an acid-producing bacterium as described above (such as AP-029, AP-044, AP-004 or AP-006) which has been engineered so as to produce urease, or a derivative of such a strain (e.g. a mutant or plasmid-carrying variant thereof).

The present invention may be more fully understood from the non-limiting Examples below and in reference to the drawings, in which:

FIG. 3 shows SEM images of sand20 biocement.

FIG. 4 shows an SEM image of sand40 biocement.

FIG. 5 shows SEM images of (a) 90% sand20 and (b) 50% sand20.

FIG. 6 shows elemental mapping of sand20 sample using EDS on SEM.

Figure 7:
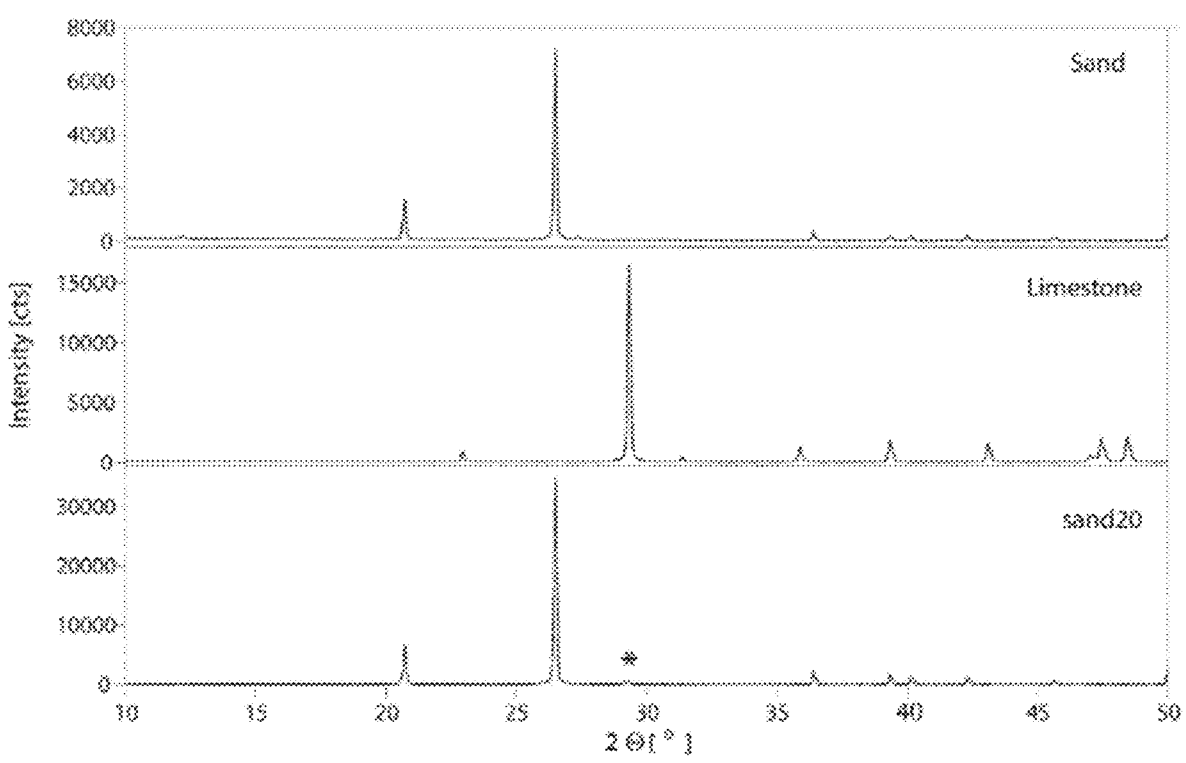

FIG. 7 XRD patterns of sand, limestone and the sand20 biocement sample.

Figure 8:
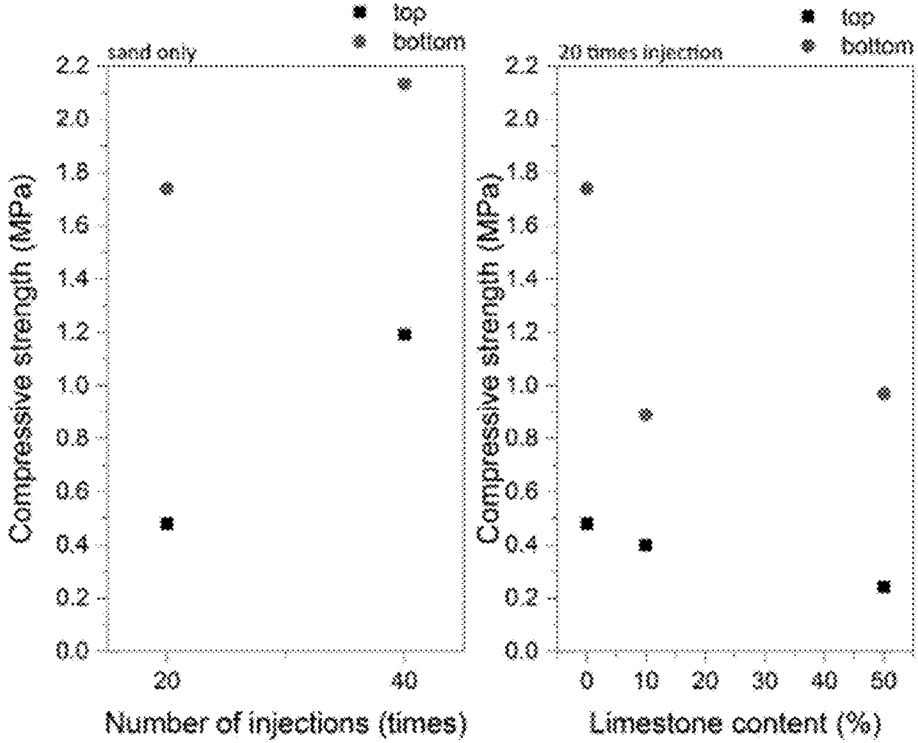

FIG. 8 shows the compressive strength of consolidated samples produced using different numbers of reagent injections and having different limestone content.

Figures 9A, 9B, 9C:
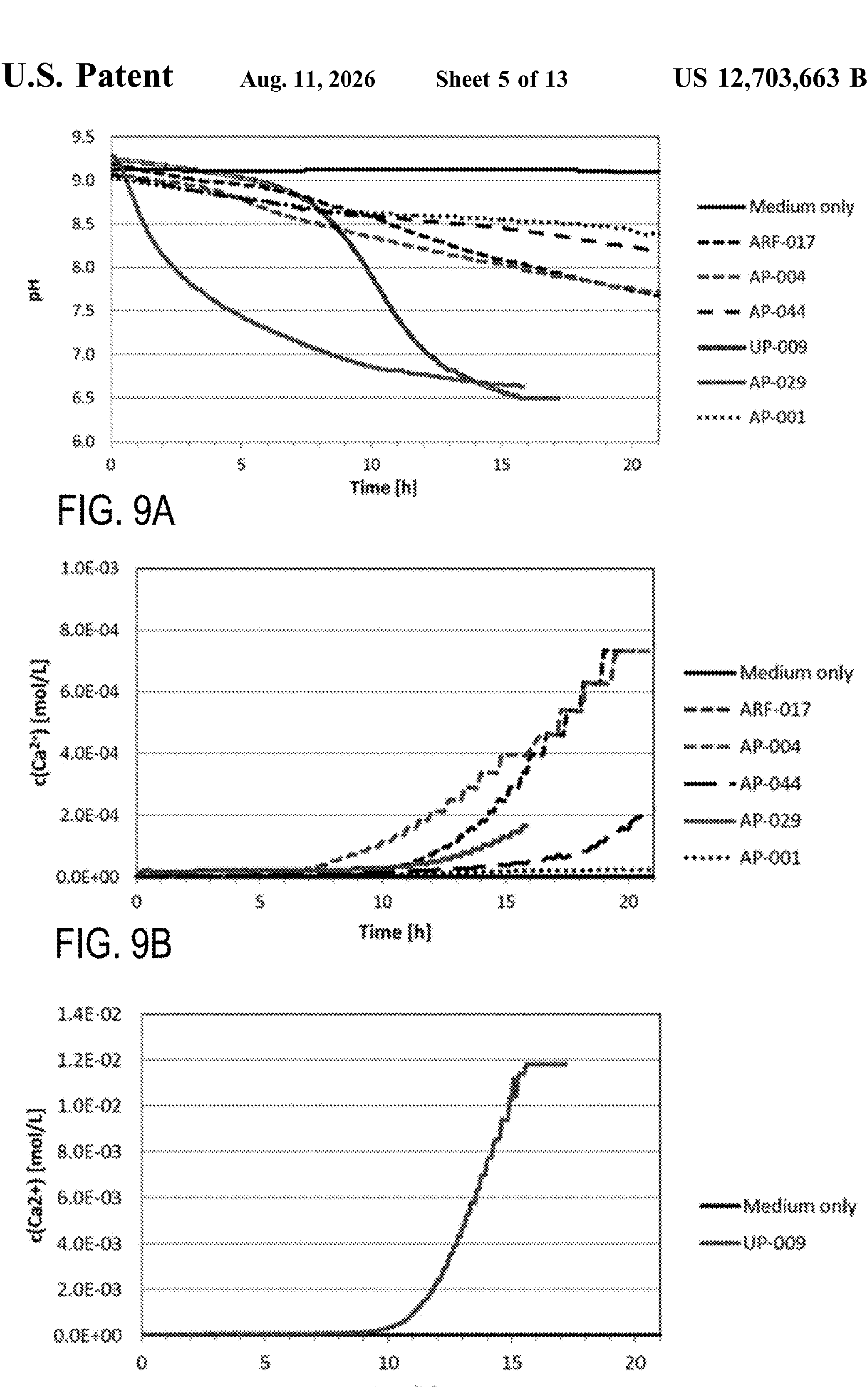

FIG. 9 shows pH (A) and $Ca^{2+}$ ion concentration development in limestone dissolution reactions containing different BSL-1 (B) and one BSL-2 strains (C) as a function of time. Experiments with AP-029 and UP-009 were carried out for about 16 hours, while experiments with the remaining strains and the negative control (medium only) were performed for about 21 hours.

Figure 10A:
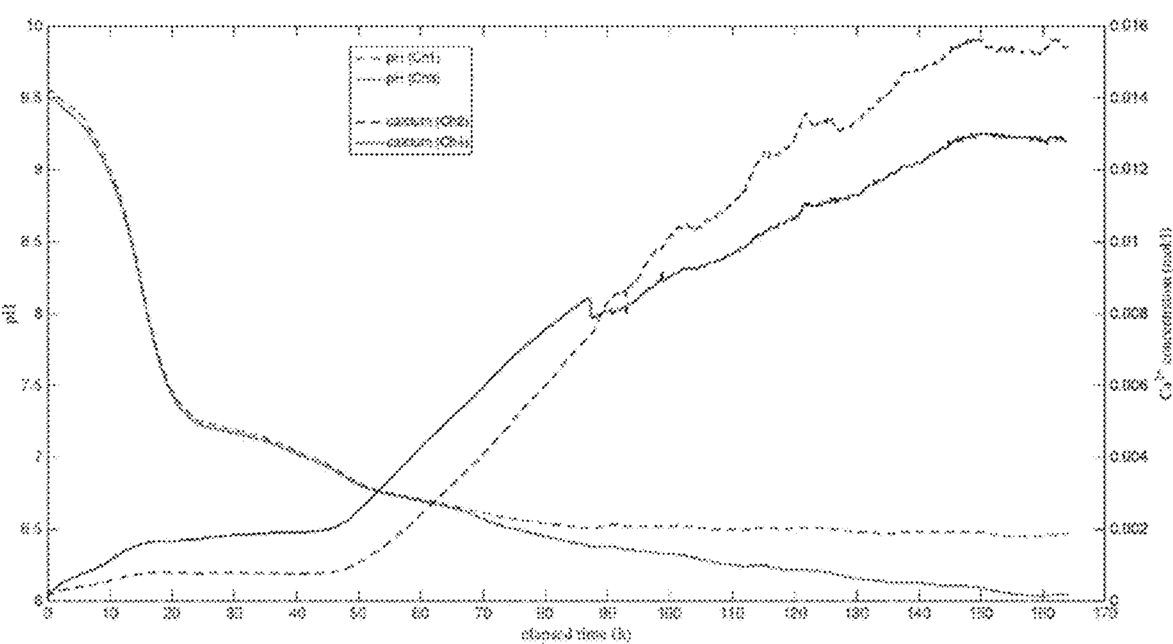
Figure 10B:
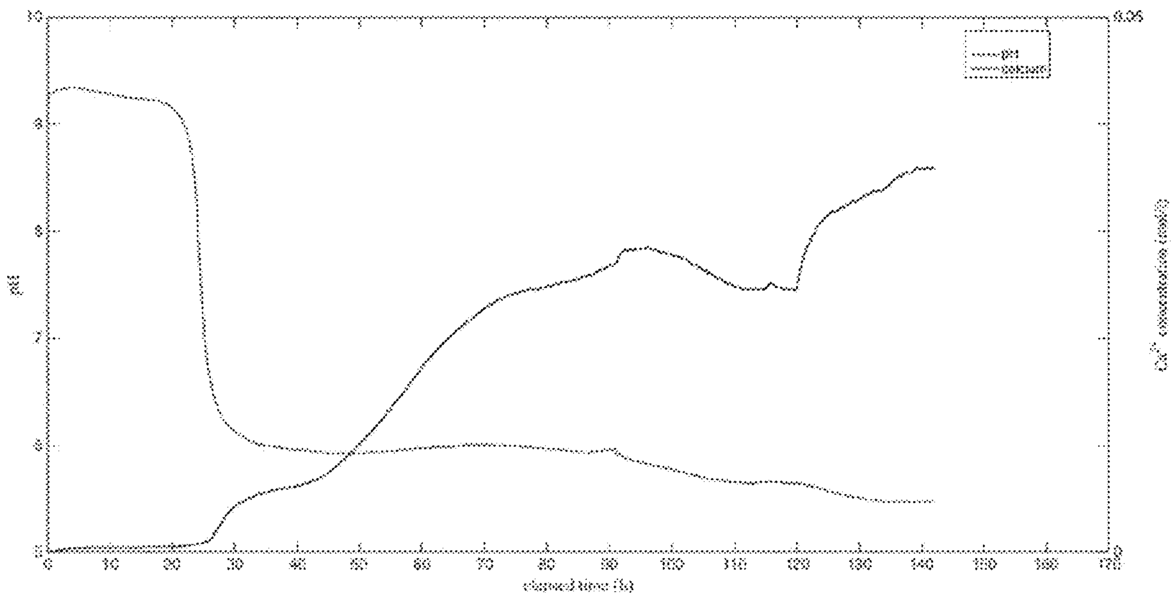

FIG. 10 shows the results of two chalk dissolution experiments using *B. safanensis* strain AP-004. Changes in the pH and $Ca^{2+}$ concentration of the solutions are shown in each graph. In part B two ISE and two pH electrodes were used in the solution; the results from each electrode are shown separately.

Figure 11A:
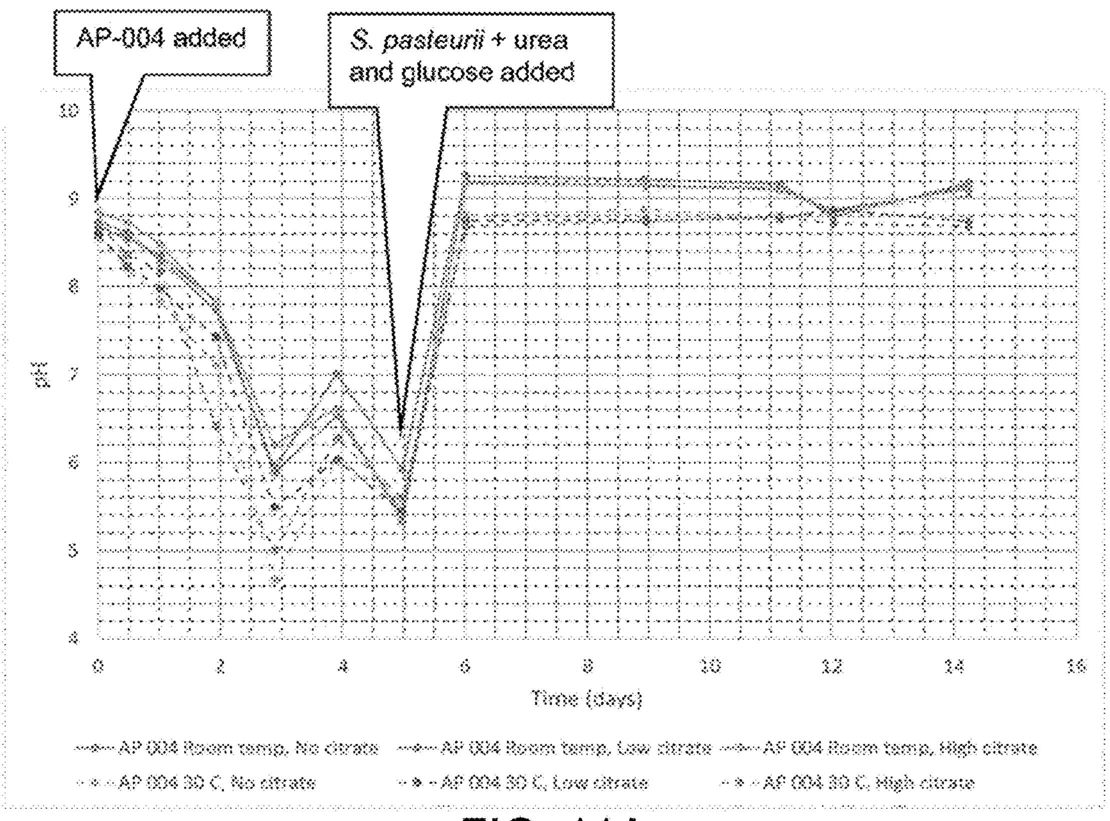
Figure 11B:
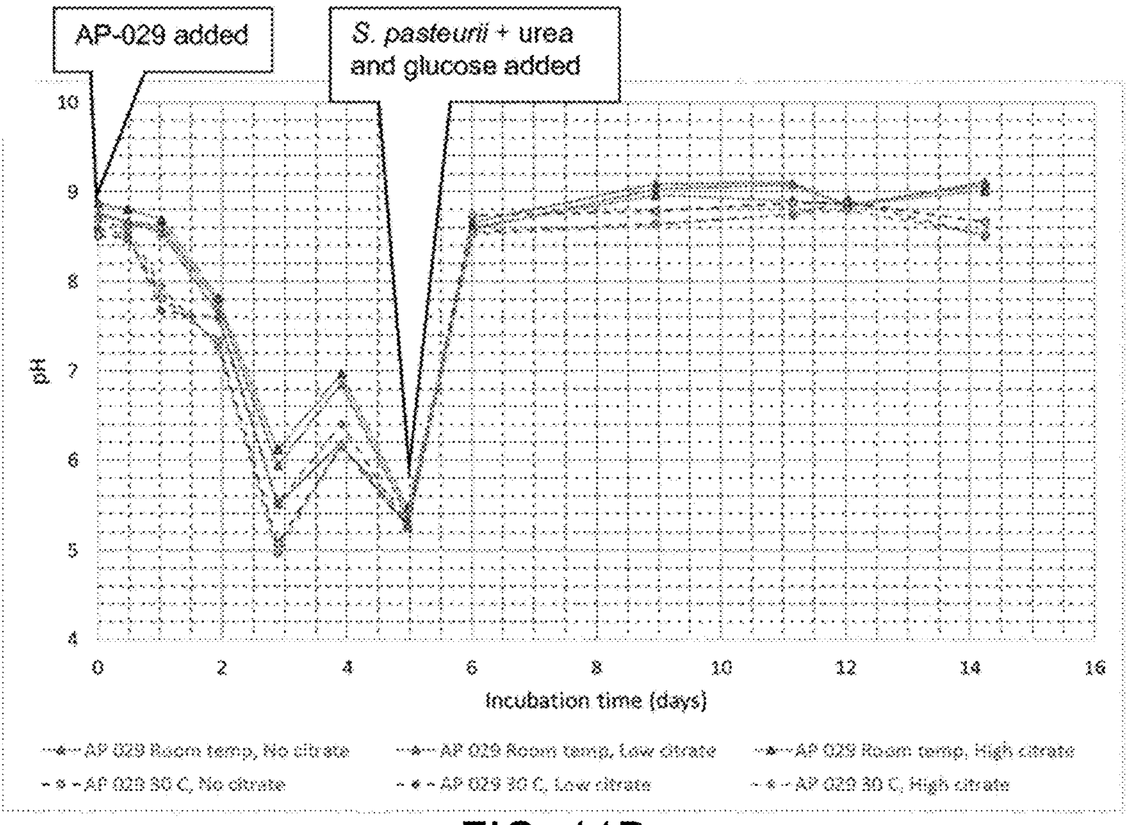

FIG. 11 shows the pH profile of chalk suspensions in defined medium following addition of acid-producing strain AP-004 (A) or AP-029 (B) and later the urease-producing species *S. pasteurii*.

Figure 12:
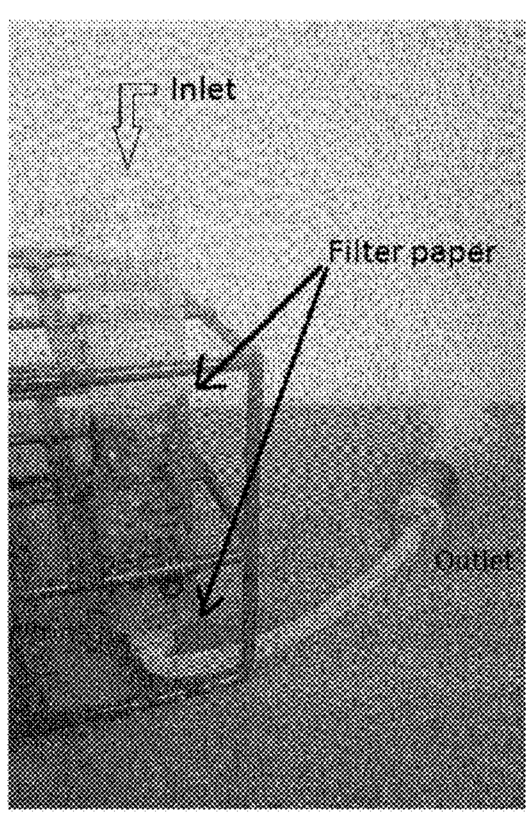

FIG. 12 shows a picture of the setup for the consolidation experiments.

Figure 13:
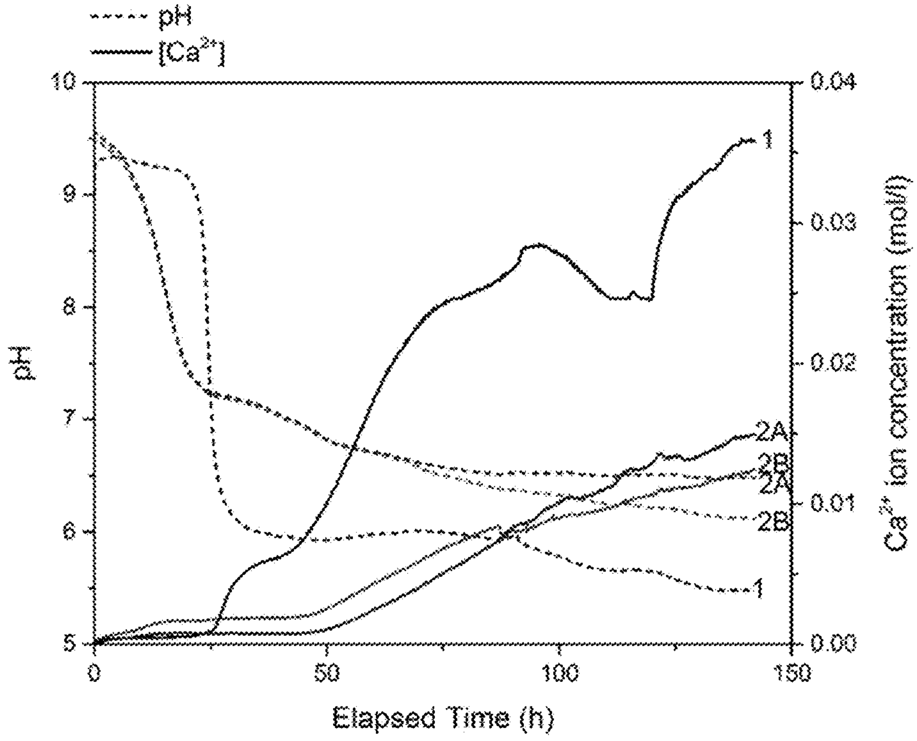
Figure 14A:
Figure 14A:
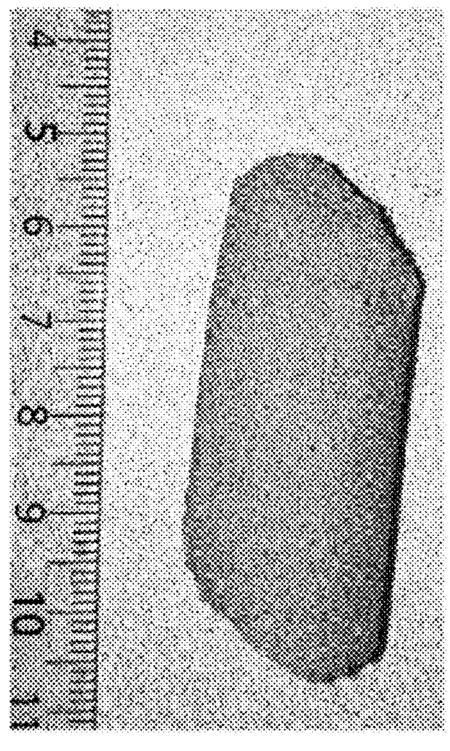
Figure 14A:
Figure 14B:
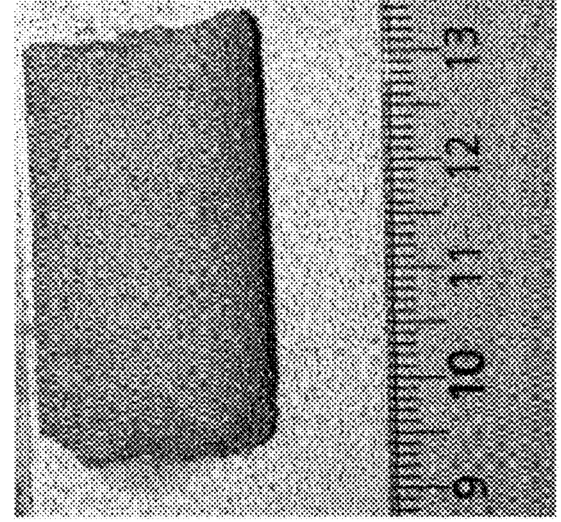

FIG. 13 shows the change over time in pH and $Ca^{2+}$ concentration of the limestone dissolution solution used in the consolidation experiment. The graph shows the results of two experiments. The results of the first experiment are labelled "1" and the results of the second experiment "2A" or "2B". The second experiment used two sets of probes (A and B), the results obtained from each of which are shown separately.

FIG. 14 shows two consolidated sand samples made using the method of the invention. The scales shown are in centimetres.

Figure 15A:
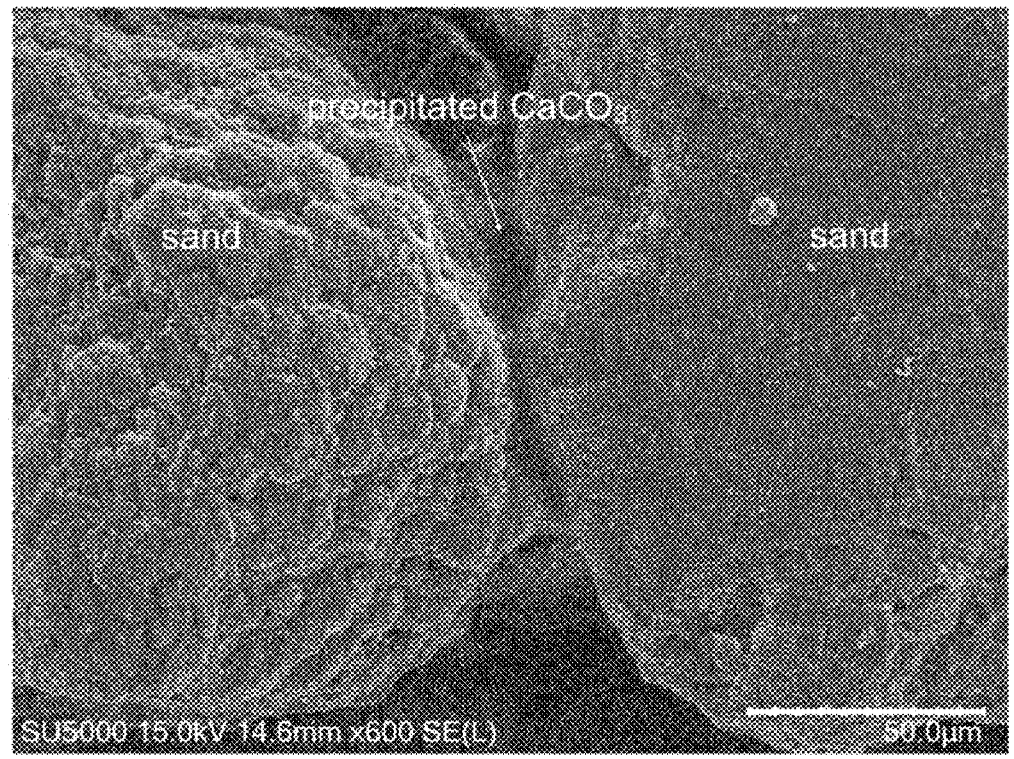

FIG. 15 shows SEM images of the first consolidated sand sample. The magnification and scale are shown at the bottom of each image.

FIG. 16 shows SEM images of the second consolidated sand sample. The magnification and scale are shown at the bottom of each image.

Figure 17A:
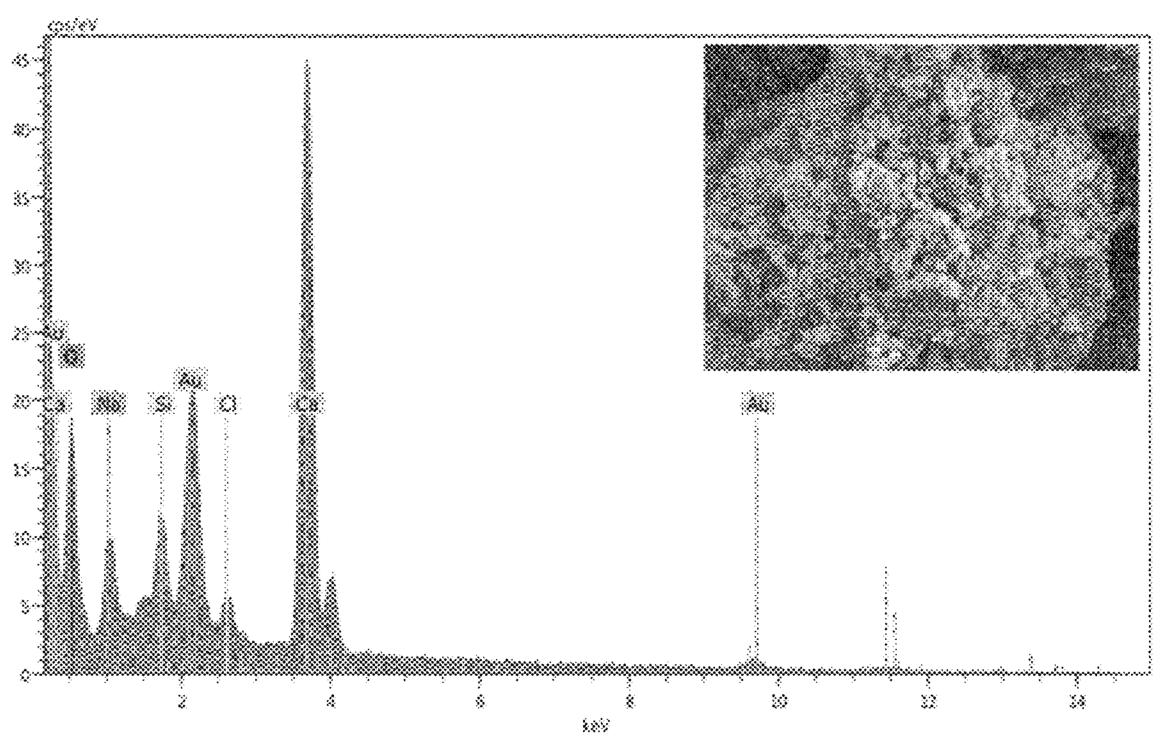
Figure 17B:
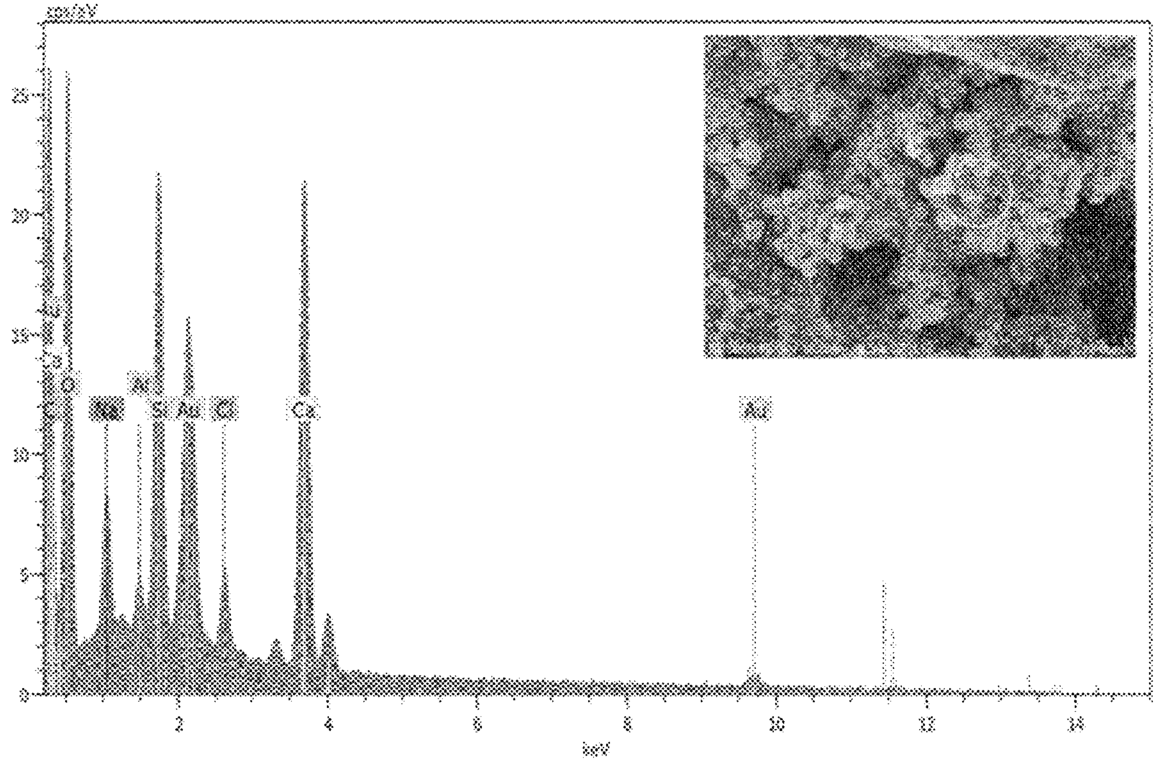

FIG. 17 shows EDS results of the precipitated crystals in the consolidated sand samples. The results from the first sample are presented in part A, and the second sample in part B.

EXAMPLES

Example 1: Proof of Concept

Materials and Methods

Materials

Sand of 50-70 mesh size from Sigma-Aldrich (USA) was used. Jack Bean (*Canavalia ensiformis*) urease used in this study was supplied by Sigma-Aldrich, with a specific activity of 50,000-100,000 units/g solid. Crushed limestone used in this study was an industrial grade chalk powder, obtained from Franzefoss Miljøkalk AS (Norway), with a density of 2.7 $kg/dm^3$ and particle size ranging from 1-200 μm.

Preparation of Reagent

Calcium-rich solution (CRS) was prepared by dissolving crushed limestone in 0.3 M lactic acid at room temperature (~20° C.) until saturation was reached. The solution was stirred using a magnetic stirrer. The amount of limestone needed in the dissolution was estimated through PHREEQC, a geochemical modelling program. According to the program, at least 15 g of limestone is required per litre of lactic acid in order to obtain a $Ca^{2+}$ saturated solution (however, as indicated above it is not necessary for the method of the invention for a saturated solution to be obtained, or used). For the purposes of this experiment, 25 g of limestone were used per litre of 300 mM lactic acid, to ensure sufficient limestone was provided. Dissolution was carried out for 24 h, with a pH and ion-selective electrode (ISE) to monitor the changes of pH and $Ca^{2+}$ ion concentration in the solution. Then, the solution was filtered through filter paper to remove the remaining non-dissolved limestone, and the CRS was obtained. Next, 0.15 M of urea was added to the CRS. $Ca^{2+}$ ion concentration was measured through atomic absorption spectroscopy (Perkin Elmer AAnalyst 400, USA).

Preparation of Bio-Cement

Bio-cement was prepared in a split mould of 25 mm diameter. First, 60 g of grains and 0.2 g of urease were mixed well. Then, the mixture was fed into the split mould, the two halves of which were held together tightly by screws. A layer of filter paper and porous flow channels were placed at the top and bottom of each mould. Next, the grains were compacted by tightening a screw and spring assembly on the top of the mould. The split mould was connected to a syringe pump at the inlet, and the outlet tube was placed in a beaker to drain the waste. A pressure sensor was placed at the inlet to monitor pressure changes throughout the experiment.

After that, 25 ml of reagent was injected into the mould at an injection rate of 0.5 ml/min. Reagent was pumped upwards (against gravity) through the sand in order to create more consistent results as it avoided preferential flow. The same amount of reagent was injected the prescribed number of times (Table 1). Injections were performed at 5 h intervals. After all the injections were complete, 50 ml of distilled water was injected to wash out all the by-products. Finally, the consolidated sample was taken out of the mould and dried in an oven for 2 h at 70° C. Then, the samples were sent for further characterization. Different processing conditions were used, as listed in Table 1 together with the sample coding.

TABLE 1

Processing conditions and material designation

| Sample code | Grains: Sand (%) | Grains: Limestone (%) | Urease | Number of injections |
|---|---|---|---|---|
| sand20 | 100 | 0 | 0.2 | 20 |
| sand40 | 100 | 0 | 0.2 | 40 |
| 90% sand20 | 90 | 10 | 0.2 | 20 |
| 50% sand20 | 50 | 50 | 0.2 | 20 |

Scanning Electron Microscopy (SEM)

Consolidated samples were observed under a Hitachi TM3000 TableTop SEM (Hitachi High-Technologies Corporation, Japan). Elements present in the samples were identified using Quantax70 energy dispersive spectroscopy (EDS).

X-Ray Diffraction (XRD) Analysis

Crystals present in the consolidated samples were identified using Rigaku MiniFlex600 X-Ray diffractometry, with a scan range from 10° to 90° and 10°/min scanning rate. The X-Ray source was Cu-Kα radiation with a wavelength of 0.154 nm.

Mechanical Test

The consolidated samples were cut into halves of similar height, in order to compare their properties at different parts. Mechanical properties of each layer were tested through uniaxial compression tests using a Zwicki-line testing machine (Zwick/Roell, Germany). A load cell of 1 kN and a cross-head speed of 10 mm/min were used.

$CaCO_3$ Content Measurement

A certain weight of consolidated sample was dried in an oven at 70° C. for 24h. The samples were repeatedly weighed until a constant weight was reached. Then, the samples were degraded in 0.1 M hydrochloric acid (HCl) at 30° C. and stirred with a magnetic stirrer. Changes in pH and $Ca^{2+}$ ion concentration were monitored by pH meter and ISE until constant values were reached, in order to ensure a full dissolution of the $CaCO_3$ crystals. The remaining solids were filtered out of the solutions using filter paper, washed several times with distilled water, dried and re-weighed. $CaCO_3$ content was determined using the following equation:

$$CaCO_3 \text{ content (wt \%)} = \frac{\text{Weight of samples before acid digestion}}{\text{Weight of samples after acid digestion}} \quad (1)$$

Porosity Measurement

Changes in porosity throughout the consolidation experiments were monitored by a pressure sensor attached to a tube connecting to the inlet of the split mould. Data on the pressure changes is able to provide information on porosity inside the mould.

Results and Discussion

Dissolution of Crushed Limestone

Figure 1:
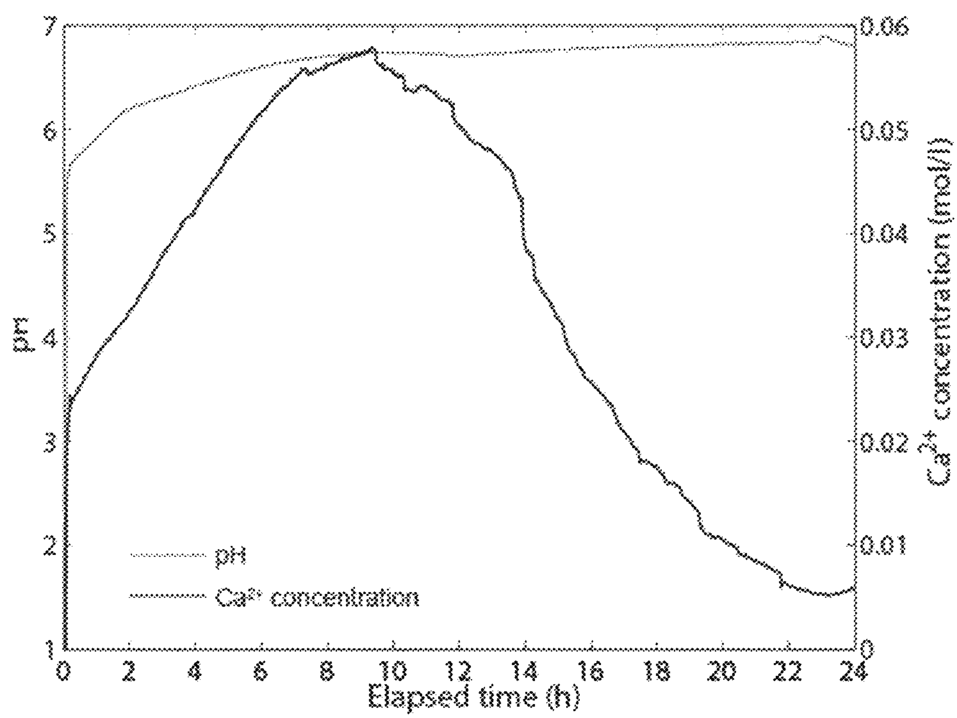
FIG. 1 shows changes of pH and $Ca^{2+}$ ion concentration over dissolution time.

During the preparation of CRS, changes of pH and $Ca^{2+}$ ion concentration were monitored throughout the dissolution process as shown in FIG. 1. It can be observed that pH increased rapidly from ~pH 2 to ~pH 5.5 within the first 10 min after the addition of limestone into lactic acid. The increase of pH is due to the consumption of hydrogen ($H^+$) ions from the lactic acid during the dissolution process, as described in the following equation:

$$CaCO_3 + \text{Lactic acid(HLac)} \rightarrow Ca^{2+} + HCO_3^- + Lac^-$$

This indicates a rapid dissolution of limestone at the initial stage. Then, the dissolution rate slowed down and reached a constant pH of 6.7 after around 9 h. This suggests that the solution reaches its saturation point after about 9 h. The concentration of $Ca^{2+}$ ions in the solution was measured as a function of time, as illustrated in FIG. 1. The $Ca^{2+}$ concentration increased rapidly with time during the first 10 min to around 0.024 mol/l, then increased at a slower rate until it reached a maximum concentration of 0.056 mol/l after 9 h. However, it was followed by a gradual decrease of $Ca^{2+}$ concentration in the solution which reached a concentration of 0.0069 mol/l at 24 h. The described phenomenon can be explained by methodological reasons. In a paper by Zander and Cooper (Intensive Care Medicine. 19(6): p.

362-363), they described the interference in $Ca^{2+}$ concentration as measured by ISE by the presence of metabolisable anions such as lactate, acetate or malate. Lactate ions are known to complex with and chelate $Ca^{2+}$ ions, causing the chelated calcium to no longer be detected by ISE. During the dissolution of limestone, $Ca^{2+}$ ion concentration increased in the solution, but at the same time chelation of calcium occurred. When the solution reached saturation point, the $Ca^{2+}$ ion concentration in the solution became constant. Meanwhile, more and more $Ca^{2+}$ ions were chelated by lactate and could thus no longer be detected by ISE. Hence, the measured $Ca^{2+}$ concentration reduced with time after the saturation point was reached at around 9 h of dissolution. This also suggests that ISEs are not suitable for the measurement of $Ca^{2+}$ concentration when lactate is present. In order to obtain an accurate measurement of the amount of dissolved calcium, the final solution was analysed by atomic absorption spectroscopy (AAS), giving a $Ca^{2+}$ ion concentration of 0.065 mol/l.

Morphological Studies

Figure 2:
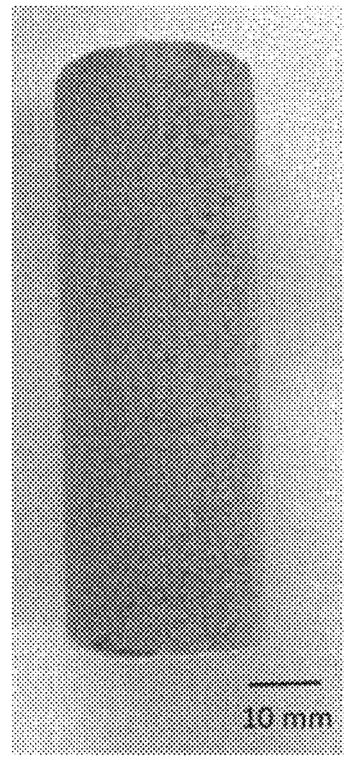
FIG. 2 shows a consolidated sample of sand20 biocement.

After the preparation of bio-cement, consolidated cylindrical samples were obtained. A typical image of a consolidated sand sample (before cutting) is shown in FIG. 2. The cylindrical consolidated samples have diameters of approximately 25 mm and heights ranging from 80-95 mm.

To confirm reproducibility, two samples were made under each processing condition. Fairly large parts of the consolidated samples were well cemented, and retained their structure even when immersed in water. This proved the feasibility of utilising the dissolution-recrystallization mechanism to achieve cementation.

FIG. 3 shows SEM images of the consolidated sand sample, sand20. From FIG. 3A it can be seen that crystals have precipitated on the free surface and in between the sand grains. These precipitated crystals act as a cement to bind the sand grains together. It is interesting to note that most of the precipitated crystals exhibit a semi-spherical morphology, as illustrated in FIGS. 3B and 3C, with a diameter ranging from 20-100 μm. From a close-up of the spherical crystal (FIG. 3D) at higher magnification, it can be observed that the spheres appeared to be spherical aggregates of smaller sub-units of around 1-5 μm. Similar crystal morphology was also observed in the sand40 samples, as shown in FIG. 4. The XRD results (which will be discussed further later) confirm that these precipitated crystals are calcite, the most stable polymorph of $CaCO_3$. Other researchers have previously reported similar $CaCO_3$ crystal morphology, which is known as spherulitic calcite (the crystals being calcite spherulites). Calcite spherulites are formed by aggregation of the typical rhombohedral calcite crystals into a spherical orientation. It is believed that the presence of organic molecules such as lactate is the main trigger of the spherulitic growth of calcite.

For 90% sand20 and 50% sand20 samples, 10 wt % and 50 wt % of sand was replaced by crushed limestone, respectively. A similar cementation effect is observed from the SEM images (FIG. 5), in which the precipitated calcite crystals act as a binder to bind the grains together. The precipitated crystals and the added limestone are both calcite, and thus are difficult to distinguish. However, on some occasions, the precipitated calcite and the limestone can be distinguished. In FIG. 5A, two distinct morphologies of calcite can be detected. Crushed limestone is known to have a rhombohedral morphology and often has facet surfaces (as labelled in the figure). Meanwhile, the precipitated crystals appear as a cluster of smaller crystals similar to those observed in sand20 and sand40 samples, but not in a spherical orientation. This can be confirmed by a visible hole that is created by a pulled-out sand grain in FIG. 5A, where the precipitated small calcite crystals formed an aggregate and covered the sand grain. For the 50% sand20 sample (5B), it is difficult to distinguish the calcite crystals because the composition of added limestone is present in a higher amount than the precipitated calcite. In both the samples with added limestone, the presence of calcite spherulites was not detected. Differences in calcite morphology between sand and sand-limestone systems are likely due to differences in the number of potential heterogeneous nucleation sites. Random orientation of precipitated calcite in the sand-limestone systems suggests that nucleation occurred too rapidly in these systems. This results in the formation of many small calcite crystals at different places, subsequently prohibiting spherulitic growth of calcite. Therefore, it is postulated that limestone provides potential nucleation sites for calcite.

Elemental Analysis and Phase Identification

Elements present in the sand20 sample were identified using EDS mapping. Distribution of different elements in the framed area is illustrated in FIG. 6. Big grains that contained silicone (Si) and oxygen (O) correspond to sand (quartz, $SiO_2$). The spherical crystal aggregates contained calcium (Ca), carbon (C) and O and are expected to be $CaCO_3$. This is further confirmed by using XRD analysis. FIG. 7 shows typical XRD patterns of bare sand, crushed limestone and the sand20 sample. Crushed limestone composed of the mineral calcite with the strongest XRD peak positioned at 2Θ of 29.3°, which is known to be calcite (104). A similar calcite peak is also observed in the sand20 sample (marked as * in FIG. 7), confirming the precipitation of calcite in the consolidated sample. Calcite content in the consolidated samples is much lower as compared to sand and thus, other lower intensity calcite peaks are not noticeable.

Mechanical Properties

The consolidated samples were cut into halves with similar heights, in order to compare their properties at different parts. As described in the experimental procedures, reagents were pumped upward into the mould during the production of bio-cement. Thus, the bottom layer is the part that was closer to the injection inlet, whereas the top layer is the part that was situated further from the injection inlet.

Results from the uniaxial compression test are presented in FIG. 8. It can be seen that the bottom layer samples give an overall higher compressive strength than the top layer samples. This is attributed to greater $CaCO_3$ precipitation at the bottom layer that is situated closer to the injection inlet, as the reagents flow in from the bottom of the mould during each injection. The region further from the injection inlet (top layer) shows lower $CaCO_3$ precipitation. Significant improvement in compressive strength is observed when the number of injections is increased from 20 to 40, for both top and bottom layer samples. This is due to greater $CaCO_3$ precipitation at the higher number of injections, as expected.

Example 2: Isolation of Acid-Producing Strains

Materials and Methods

Samples, Growth Media and Isolation of Strains

Soil samples were collected near an open quarry for $CaCO_3$ in Tromsdalen, a side-valley to Verdalen, Nord-Trøndelag, Norway. Sterile water was added to the samples at 1-2.5 ml/g sample (depending on the character and original water content of the sample), samples shaken vigorously to extract free-living microorganisms associated with the material and filtered through a tea strainer to remove larger particles. The resulting water extracts of the samples were heated for 10 min at 75-82° C. in order to select for spore forming microorganisms. Samples were frozen at −20° C. and freeze-dried prior to further use. For strain isolations, 1 g freeze-dried material was added to 10 mL water and stirred vigorously. An aliquot of this was used to prepare a 10-fold dilution in water for subsequent inoculation of two types of agar plates to identify acid producing microorganisms and microorganisms positive for production of the enzyme urease. For discovery of alkaliphilic, acid-producing strains, RM-9.5 medium was used (1.0 g/L yeast extract (Oxoid), 3.0 g/L peptone (Oxoid), 10.0 g/L glucose, 5.0 g/L NaCl, 2.5 ml/L thymol blue solution (1% w/v), 15 g/L agar; the pH was adjusted to 9.5 using 1.2 g/L $Na_2CO_3$). Microbial acid production resulted in the colour of the plates changing from blue to yellow. For isolation of urease positive strains, Christensen urea medium was used (Urease Test Protocol—Benita Brink: http://www.microbelibrary.org/library/laboratory+test/3223-urease-test-protocol; 1.0 g/L peptone (Oxoid), 10 g/L glucose, 5.0 g/L NaCl, 2.0 g/L $KH_2PO_4$, 20.0 g/L urea, 0.012 g/L phenol red, 15 g/L agar; the pH was adjusted to 6.5 using 1 M NaOH). Microbial production of urease resulted in the colour of the plates changing from yellow to red.

Agar plates were incubated at 30° C. for up to 7 days, and in order to obtain pure isolates, colonies corresponding to the desired acid or urease production phenotype, respectively, were picked as they appeared and plated on new agar plates and incubated at 30° C. until colonies appeared. From plates with pure isolates, one single colony was picked and transferred to a 12-well plate (Costar 3513) containing 1.2 ml of the medium used in the respective type of enrichment/isolation, and incubated in a shaking incubator at 30° C., 85% humidity, and 250 rpm. Cultures growing in the 12-well plates were harvested after 5 days of incubation and used as an inoculum for shake flask cultures, as well as for analyses on agar plates. The shake flask cultures were incubated shaking at 30° C. and 150 rpm, the agar plates as described above. Samples from the shake flasks were supplemented with 15% glycerol (v/v, final concentration), and agar plate cultures were harvested using 5 mL of the respective growth medium containing 15% glycerol. The glycerol cultures were stored at −80° C.

Analytical Methods

Acid production and urease activity in liquid culture and on agar plates were qualitatively detected by colour change of the pH indicators included in the medium (see above). For quantification of acids produced and glucose utilised, HPLC analysis was performed. HPLC analyses were carried out using a Shimadzu HPLC equipped with an HPX-87H Aminex column using 5 mM $H_2SO_4$, flow rate 0.6 ml/min at 45° C. Bacterial culture growth was monitored using optical density measurements at 660 nm wavelength with a Shimadzu UV-1800 spectrophotometer. Taxonomic analysis was carried out by PCR amplification and sequencing of the 16S rRNA gene followed by bioinformatic classification of the gene sequence. PCR amplification was carried out using "Expand High Fidelity PCR system" from Roche. The isolates were grouped according to BLAST homology analyses' closest hit and ranged within groups based on acid production and growth phenotype.

Limestone Dissolution Experiments

Pre-cultures were prepared in 9 cm petri dishes containing an agar layer made of solid RM-9.5 medium with 30 g/L glucose, topped with 10 mL liquid RM-9.5 medium with 30 g/L glucose. 15 µl cell suspension from glycerol stocks was used as inoculum and the pre-culture incubated stationary at 30° C. When the medium turned yellow (indicating pH decrease due to acid production) and turbidity was observed (indicating culture growth), 1 mL of the liquid phase was transferred to 25 mL fresh RM-9.5 medium containing 30 g/L glucose and 10 g/L $CaCO_3$ powder in 50 ml tubes, and placed for 1-3 days at 30° C. in tilted racks in a shaking incubator at 200 rpm.

For limestone dissolution experiments, 15 g of $CaCO_3$ powder was mixed with 6 mL RM-9.5 medium containing 30 g/L glucose and 10 g/L $CaCO_3$ in 50 mL tubes, to which 120 µl bacterial culture was added. A respective setup without bacterial culture added was used as a negative control. Calibrated pH and $Ca^{2+}$ electrodes (ELIT electrodes, NICO2000) were placed inside the tube, the opening was sealed with Parafilm to prevent evaporation, and continuous measurements were performed every 5-10 minutes for 16-21 hours using the ELIT 4-channel Ion-Analyzer with its corresponding software.

Results and Discussion

Screening and Selection of Strains

From processing of five soil samples, a strain collection of in total 65 isolates was established, consisting of 41 isolates from acid-production screening and 24 from urease-activity screening. The individual pure strains were arrayed in the wells of a 96-well microtiter plate, representing a master plate for subsequent analyses and selection of the best performing strains.

The microbial isolates were analysed and selected for properties useful for the production of bio-cement according to the method of the invention, in particular the ability to grow and produce high levels of acids at reduced oxygen level and high pH associated with the presence of high concentrations of limestone. Growth, acid production and urease activity on solid and/or liquid medium were tested, as well as performance in the presence of $CaCO_3$ powder in the medium and at low oxygenation. In addition, isolates were taxonomically classified using 16S rRNA gene sequence analysis.

Of the 65 strains of the strain collection, 13 strains (Table 2) were selected as potential candidates for use in Bio-cement application testing based on their ability to grow at high pH and the production of significant amounts of acid. Two of these strains (UP-009, URF-016), derived from urease screening, were in addition confirmed for their ability to produce and secrete urease. All 13 strains were able to grow and produce acid at reduced oxygen levels and in the presence of limestone powder in the medium. Surprisingly, the addition of limestone to the growth medium enhanced glucose utilization and total acid production. The total acid production of the strains was in the range of 32-75 mM acid, with lactic acid being the dominant acid, constituting 70-80% of the total acid produced. In addition, acetic acid and minor amounts of succinic acid were detected.

Taxonomic analysis of the strains revealed that the strains were all related to different species of the genera *Bacillus/Jeotgalibacillus*, which are known to contain spore-forming environmental strains. Three strains (ARF-002, UP-009, URF-016), were found to be closest related to strains that were previously described as human pathogenic species related to food poisoning and therefore require handling at Biosafety level 2, unlike the residual strains that were closest related to harmless species. Six of the 13 strains were selected for tests for their capability to dissolve limestone in high solids reactions.

TABLE 2

Strains selected as potential candidates for use in bio-cement application testing. Total acid produced was determined by end-point measurements. Strains in bold were selected for limestone dissolution tests.

| ID | Closest relative based on 16S rRNA gene sequence | Total acid produced (mM) | Biosafety level (BSL) |
|---|---|---|---|
| **AP-001** | ***Jeotgallibacillus soil*** | **32** | **1** |
| ARF-002 | *Bacillus mycoides/ Bacillus weihenstephanensis* | 75 | 1/2 |
| **AP-004** | ***Bacillus safenensis*** | **37** | **1** |
| AP-005 | *Bacillus pumilus* | 65 | 1 |
| AP-006 | *Bacillus simplex* | 69 | 1 |
| AP-007 | *Bacillus pumilus* | 75 | 1 |
| AP-011 | *Bacillus pumilus* | 35 | 1 |
| AP-024 | *Bacillus pumilus* | 34 | 1 |
| **AP-029** | ***Bacillus pumilus*** | **35** | **1** |
| **AP-044** | ***Bacillus licheniformis*** | **60** | **1** |
| **ARF-017** | ***Bacillus safenensis*** | **38** | **1** |
| **UP-009** | ***Bacillus weihenstephanensis*** | **62** | **2** |
| URF-016 | *Bacillus cereus* | 65 | 2 |

Limestone Dissolution Experiments

Six of the 13 strains were selected for tests for their capability to dissolve limestone in high solids reactions. The tests showed that all of these strains were capable of reducing the pH in the reactions and releasing $Ca^{2+}$ from the limestone powder. Both pH and $Ca^{2+}$ concentration evolution profiles were significantly above background level, determined by a negative control reaction, containing medium only (FIG. 9). However, the strains displayed different behaviour in both acid production (observed as decrease in pH) and dissolution of limestone (observed as increase in free $Ca^{2+}$ ions). Within a period of 16-21 hours of continuous measurements, the BSL-2 strain UP-009 was clearly the best total acid producer, resulting in the highest free $Ca^{2+}$ concentration and the lowest pH. Among the BSL-1 strains, ARF-017 and AP-004 performed best in limestone powder dissolution in that period. However, the amount of $Ca^{2+}$ ions released by these strains was approx. an order of magnitude smaller than by the UP-009 strain in that time period. The remaining three strains (AP-001, AP-024 and AP-044) started to dissolve limestone later than the first three and continued to produce acid when the experiment was stopped.

Example 3: Preparation of Dissolved Chalk Solutions Using *B. safenensis* AP004

Materials and Methods

Inoculum of *B. safanensis* strain AP-004 was prepared in rich medium from a culture grown on an agar plate. 40 g of chalk was added into 1 L rich medium already containing 10 g/L $CaCO_3$ (rich medium (RM): glucose.$H_2O$ 33 g/L, NaCl 5 g/L, $Na_2CO_3$ 4 g/L, peptone 3 g/L, yeast extract 1 g/L, thymol blue (1% w/v) 2.5 ml/L (i.e. resultant concentration of 0.0025% w/v), pH 9.5 (10 g/L $CaCO_3$ added after pH adjustment) in a beaker, and mixed well using a magnetic stirrer.

30 ml of AP-004 inoculum was added to the mixture. The mixture was continuously stirred using a magnetic stirrer. Changes in pH and $Ca^{2+}$ ion concentration were monitored using pH/ISE electrodes.

Results and Discussion

The results of two experiments are presented. The pHs of the solutions decreased and the $Ca^{2+}$ ion concentrations of the solutions increased with time, indicating dissolution of chalk by the acid produced by the AP-004 bacteria. The pHs dropped from their initial levels of 9.5 to 5.5-6.5 due to acid production. Results in terms of the $Ca^{2+}$ ion concentrations were slightly inconsistent between individual experiments, but both showed the same trend. The results of the two exemplary experiments are shown in FIG. 10.

Example 4: Production of a Defined Medium for Acid-Producing Strains

Background

Use of a complex medium for acid production, containing relatively large amounts of glucose as well as yeast extract and peptone, was found to have the disadvantage that after acidification and subsequent re-alkalization of the solution with *S. pasteurii*, there were still significant amounts of organic substrate, possibly including glucose, left in the solution, and a secondary re-acidification phase was thus occasionally observed as the leftover glucose was metabolised.

A chemically defined medium based on pure chemical compounds such as glucose, mineral salts ($NH_4Cl$, $K_2HPO_4$, $MgSO_4$, etc.) and if necessary limited amounts of organic growth factors (vitamins, specific amino acids, etc.), has the advantage that, if supplied in the right quantities, the only available carbon source after the acidification step will be organic acids. Any secondary growth on organic acids will lead to a pH increase, thus fortifying the pH increase due to hydrolysis of urea by *S. pasteurii.*

Materials and Methods

Bacterial Strains

Four acid-producing (AP) isolates were selected for the study. They have been assigned to species as follows: AP-004—*Bacillus* sp. closely related to *B. pumilus* and *B. safanensis*; AP-006—*Bacillus* sp. closely related to *B. simplex*; AP-029—*B. pumilus*; and AP-044—*B. licheniformis*. All are believed to be Biosafety level 1. All were cultured at 30° C. For the alkalization step *Sporosarcina pasteurii* DSM 33 was used.

Culture Media

Defined Medium 1 (DM1): Taurine 12.5 g/L; glucose.$H_2O$ 11.0 g/L; $NH_4Cl$ 2.3 g/L; trisodium citrate.$2H_2O$ 1.0 g/L; $K_2HPO_4$, 0.70 g/L; $MgSO_4.7H_2O$ 0.40 g/L; trace mineral solution 1 (TMS1, see below), 5 ml/L; Wolfe's vitamin solution (WVS, see below) 10 ml/L, pH 9.5.

Defined Chalk Suspension Medium (DCSM): Glucose.$H_2O$ 11.0 g/L; $NH_4Cl$ 2.3 g/L; $K_2HPO_4$ 0.70 g/L; $MgSO_4.7H_2O$ 0.40 g/L; TMS1 5 ml/L; WVS 10 ml/L; trisodium citrate.$2H_2O$ 0 g/L, 0.2 g/L or 1.0 g/L. One part medium was mixed with two parts chalk ($CaCO_3$).

Semi-Defined *pasteurii* Medium (SDM): Urea 20 g/L; taurine 6.25 g/L; glucose.$H_2O$ 5.5 g/L; $NH_4Cl$ 2.3 g/L; trisodium citrate.$2H_2O$ 1.0 g/L; vitamin-reduced casamino acids 1.0 g/L; $K_2HPO_4$ 0.70 g/L; $MgSO_4.7H_2O$ 0.40 g/L; trace mineral solution 1 for *S. pasteurii* (TMS1-*pasteurii*, see below) 5 ml/L; WVS 10 ml/L, pH 9.5.

Complex Medium for *S. pasteurii* (CM): Bacto™ Tryptone 15.0 g/L; Bacto™ Soytone 5.0 g/L; NaCl 5.0 g/L; urea 20 g/L; pH 7.3.

Rich Medium for AP Strains (RM): as defined above in Example 3.

Defined *pasteurii* Concentrate (DC): Glucose.$H_2O$ 55 g/L; urea 20 g/L; vitamin-reduced casamino acids 10 g/L; TMS1-*pasteurii* 5 ml/L.

WVS: Folic acid 20 mg/L; pyridoxine.HCl 10 mg/L; thiamine.HCl 5 mg/L; riboflavin 5 mg/L; nicotinic acid 5 mg/L; calcium D-(+)-pantothenate 5 mg/L; p-aminobenzoic acid 5 mg/L; thioctic acid 5 mg/L; biotin 2 mg/L; vitamin B12 0.10 mg/L.

TMS1: $FeSO_4.7H_2O$ 5.0 g/L; $ZnSO_4.7H_2O$ 0.44 g/L; $CuSO_4.5H_2O$ 0.39 g/L; $MnCl_2.2H_2O$ 0.15 g/L; $CoSO_4.7H_2O$ 20 mg/L; $Na_2MoO_4.2H_2O$ 10 mg/L; conc. HCl 50 ml/L.

TMS1-*pasteurii*: As above for TMS1 with additional 0.5 g/L $NiCl_2.6H_2O$.

Experimental Procedures

The ability of the AP isolates to grow in DM1 was screened in 8-well tissue culture plates. Cells from RM agar were inoculated into wells with 5 ml DM1 with and without 1.0 g/L casamino acids and with a varying concentration of taurine (3-100 mM). Growth was assessed visually and pH recorded as a function of time.

The ability of strains able to grow in DM1 without addition of casamino acids to acidify chalk suspensions in DM1 (without taurine) was characterised in plastic containers (120 ml) closed with a screw cap. The strains were cultured in shake flasks at 30° C. in DM1 with 100 mM taurine as buffer, harvested by centrifugation, washed once with DM1 without taurine, and inoculated into the chalk suspensions. pH was measured as a function of time at room temperature (22-23° C.) and 30° C.

The acidic chalk suspensions were re-alkalized by addition of *S. pasteurii* and DC, and the pH in the re-alkalized chalk suspension followed for 25 days. *S. pasteurii* was cultured in shake flasks at 30° C. in SDM, harvested by centrifugation, washed once with water, and inoculated into the acidic chalk suspensions. The studies were performed at room temperature and 30° C.

Results

Ability of Acid-Producers to Grow in Defined Mineral Medium

All fours strains grew well and lowered pH in DM1 when it contained 1.0 g/L casamino acids, but only two of the strains, AP-004 and AP-029, grew well and lowered pH without casamino acids in the medium. Interestingly, a small amount of $CaCl_2$ (1 mmol/L) in the medium appeared to stimulate the growth of the cells. It was also observed that cell growth rate increased when the buffer capacity was reduced, indicating that the cells grow better at a lower pH than 9-9.5. In wells with the highest buffer capacity (100 mM Taurine), pH did not decrease below pH 8.2-8.3.

When culturing bacteria at pH 9-9.5, significant amounts of ammonium in the medium may be lost to the atmosphere as ammonia. The ability of AP-004 and AP-029 to use nitrate ($NO_3^-$) instead of ammonium ($NH_4^+$) as a nitrogen source was therefore tested. Both strains could utilize nitrate as N-source, although they grew more rapidly with ammonium as N-source.

Acidification of Chalk Suspensions

The acidification of a chalk suspension in DM1 was tested using AP-004 and AP-029. DCSM (20 ml) was mixed with 40 g chalk powder in a plastic container (120 ml) closed with a screw cap. The suspension was inoculated with 0.5 ml washed cell concentrate made by centrifuging down the cells in 50 ml shake flask culture cultured in DM1, washing the cells once with sterile water and re-suspending them in 5 ml sterile water. The inoculated suspensions were incubated without shaking or stirring at room temperature and 30° C. During the next 3-5 days pH decreased to below pH 6 (FIG. 11).

Re-Alkalization of Chalk Suspensions with *S. pasteurii*

After acidification of the chalk suspensions with acid-producing bacteria, to the chalk suspensions were added 2.0 ml DC, 100 μl TMS1-*pasteurii* and a 10 times concentrated washed culture of *S. pasteurii* cultured in SDM. This was added within an hour of the pH measurement on day 5, and resulted in a rapid increase in pH to around pH 9 (FIG. 11). The pH in the suspension remained high for several weeks (Table 3).

Conclusions

A defined mineral medium with glucose as the only C-source for the acidification of chalk suspensions has been designed. The medium is suitable for use with the two isolated acid-producing strains AP-004 and AP-029. When the acidic chalk suspensions (pH 5-6) were re-alkalized with *S. pasteurii*+urea, pH remained stable at around pH 9 for weeks, and no secondary acidification phase was observed. This is in contrast to the previously employed complex medium, where a second, and unwanted, acidification phase occurred.

TABLE 3

| | Days after addition of *S. pasteurii* + urea | | | | |
|---|---|---|---|---|---|
| | 1 | 4 | 6 | 9 | 25 |
| Sample | | | pH | | |
| AP 004 Room temp. (22-23° C.), No citrate | 9.18 | 9.15 | 9.11 | 9.11 | 9.06 |
| AP 004 Room temp. (22-23° C.), Low citrate (0.2 g/L) | 9.26 | 9.22 | 9.17 | 9.18 | 9.02 |
| AP 004 Room temp. (22-23° C.), High citrate (1.0 g/L) | 9.19 | 9.14 | 9.10 | 9.14 | 9.02 |
| AP 004 30° C., No citrate | 8.81 | 8.88 | 8.77 | 9.04 | 8.96 |
| AP 004 30° C., Low citrate (0.2 g/L) | 8.75 | 8.76 | 8.77 | 8.74 | 9.00 |
| AP 004 30° C., High citrate (1.0 g/L) | 8.68 | 8.74 | 8.80 | 8.68 | 9.15 |
| AP 029 Room temp. (22-23° C.), No citrate | 8.66 | 9.09 | 9.10 | 9.11 | 8.60 |
| AP 029 Room temp. (22-23° C.), Low citrate (0.2 g/L) | 8.58 | 9.03 | 9.08 | 9.07 | 8.79 |
| AP 029 Room temp. (22-23° C.), High citrate (1.0 g/L) | 8.60 | 8.96 | 8.90 | 9.01 | 8.88 |
| AP 029 30° C., No citrate | 8.73 | 8.78 | 8.87 | 8.66 | 9.30 |
| AP 029 30° C., Low citrate (0.2 g/L) | 8.54 | 8.64 | 8.74 | 8.50 | 9.04 |
| AP 029 30° C., High citrate (1.0 g/L) | 8.52 | 8.63 | 8.75 | 8.52 | 9.23 |

Example 5: Consolidation of Sand Grains by AP-004 and *S. pasteurii* Strains

Materials and Methods

Materials

Sand with 50-70 mesh particle size from Sigma-Aldrich was used in the consolidation experiment. Crushed limestone used in this study is an industrial grade chalk powder, which is obtained from Franzefoss Miljøkalk AS, with a density of 2.7 kg/dm$^3$ and particle size ranging from 1-200 μm.

Limestone Dissolution

AP-004 bacteria were cultured in RM at pH 9.5, and used as the inoculum. 40 g of crushed limestone was added into 1 L of RM (pH 9.5) with 30 ml of AP-004 inoculum. The mixture was stirred using a magnetic stirrer, and the pH and $Ca^{2+}$ ion concentration were monitored using a pH/ISE meter. The mixture was stirred for 2-3 days, until the point where no significant changes in the pH and $Ca^{2+}$ ion concentration were observed. Next, the remaining limestone particles and bacteria were filtered out using a 0.22 μm vacuum filtration set. Then, the filtrate was used as the calcium source for the $CaCO_3$ precipitation. The filtrate is referred to herein as the dissolved chalk solution (DCS).

Preparation of Reagent

Freeze-dried *S. pasteurii* (SP) bacterial powder was cultured in CM overnight. The SP bacterial inoculum was diluted 10 times using fresh CM before use. Then, the diluted SP bacterial solution was mixed with the DCS at a ratio of 1:1. The mixture was used as the reagent in the consolidation experiment.

Consolidation Experiment

A simple setup as shown in FIG. 12 was used in the consolidation experiment. First, a 20 ml syringe was filled with sand. Filter paper was placed both on the top and the bottom of the syringe to prevent grain loss during the experiment. Then, 6 ml of reagent was added from the top of the syringe (inlet). The reagent was drawn downwards to fill up the syringe using another syringe that was attached at the outlet. The reagent was kept in the syringe for at least 3 h before fresh reagent was added. This process was repeated 20 times.

Results

In this work, a pH/ISE meter was used to keep track of the limestone dissolution process. FIG. 13 shows the changes of pH and $Ca^{2+}$ ion concentration of the mixture. Limestone dissolution is confirmed through the reduction in pH and increase in $Ca^{2+}$ ion concentration of the mixture. DCS with a final pH ranging from pH 5.5-pH 6.5, and a final $Ca^{2+}$ ion concentration ranging from 0.022-0.035 mol/l, was used in the consolidation experiment.

Through the consolidation experiment, two consolidated sand samples were successfully produced, which are shown in FIG. 14. Most of the sand was well cemented, and the blocks retained their structures even when immersed in water. This proves the feasibility of utilizing DCS produced by AP-004 and SP strains to achieve cementation.

Figure 15B:
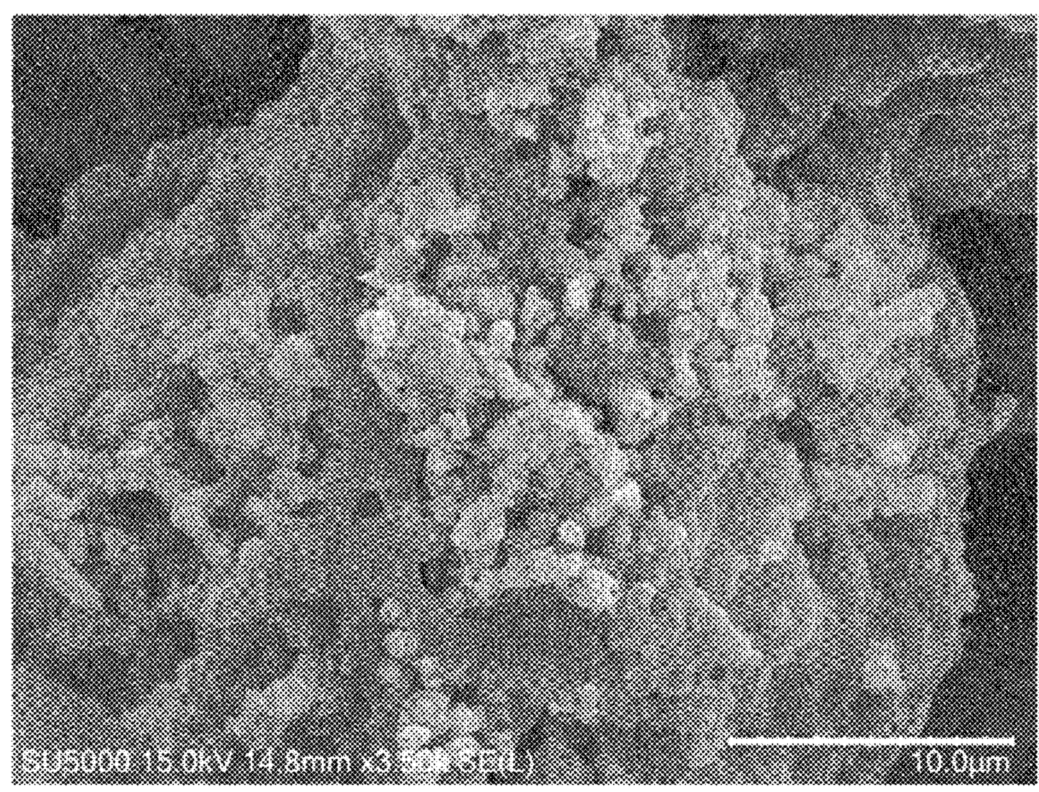
Figure 15C:
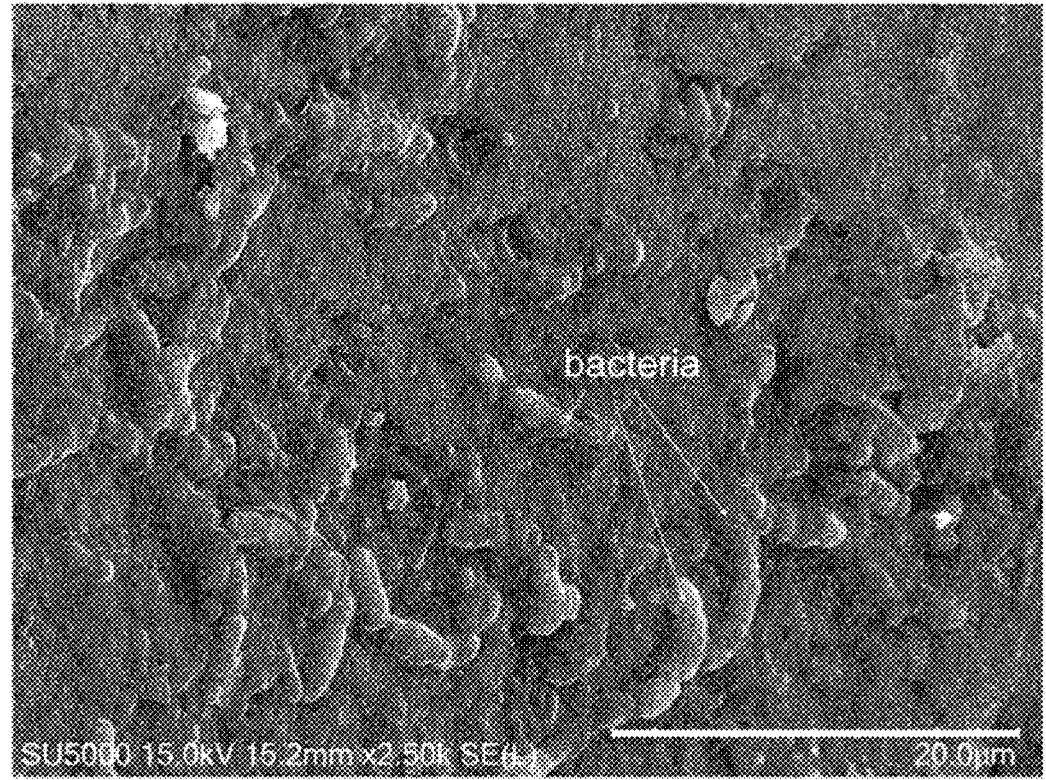
Figure 16A:
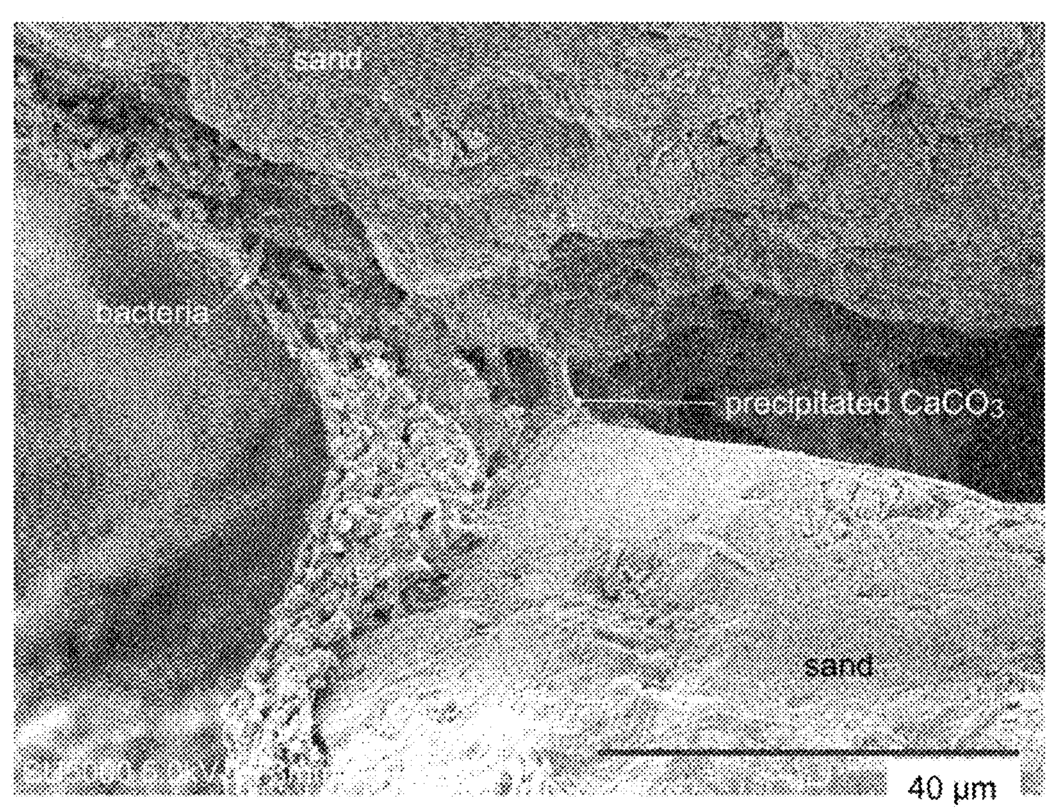
Figure 16B:
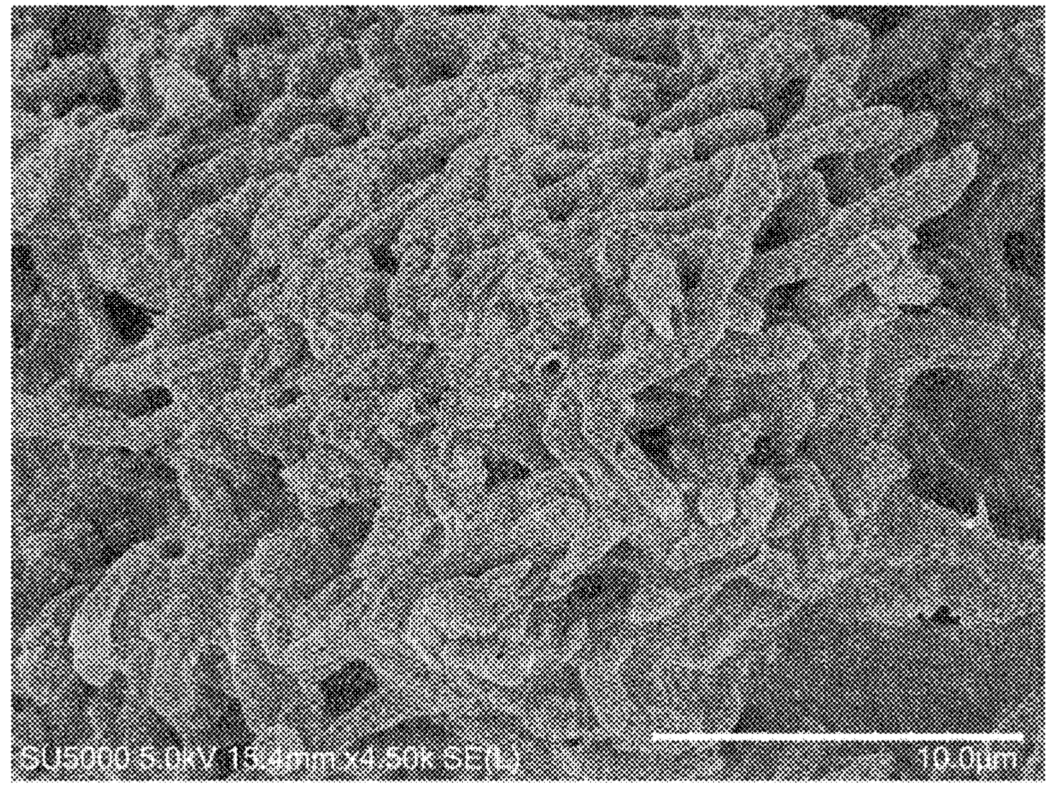
Figure 16C:
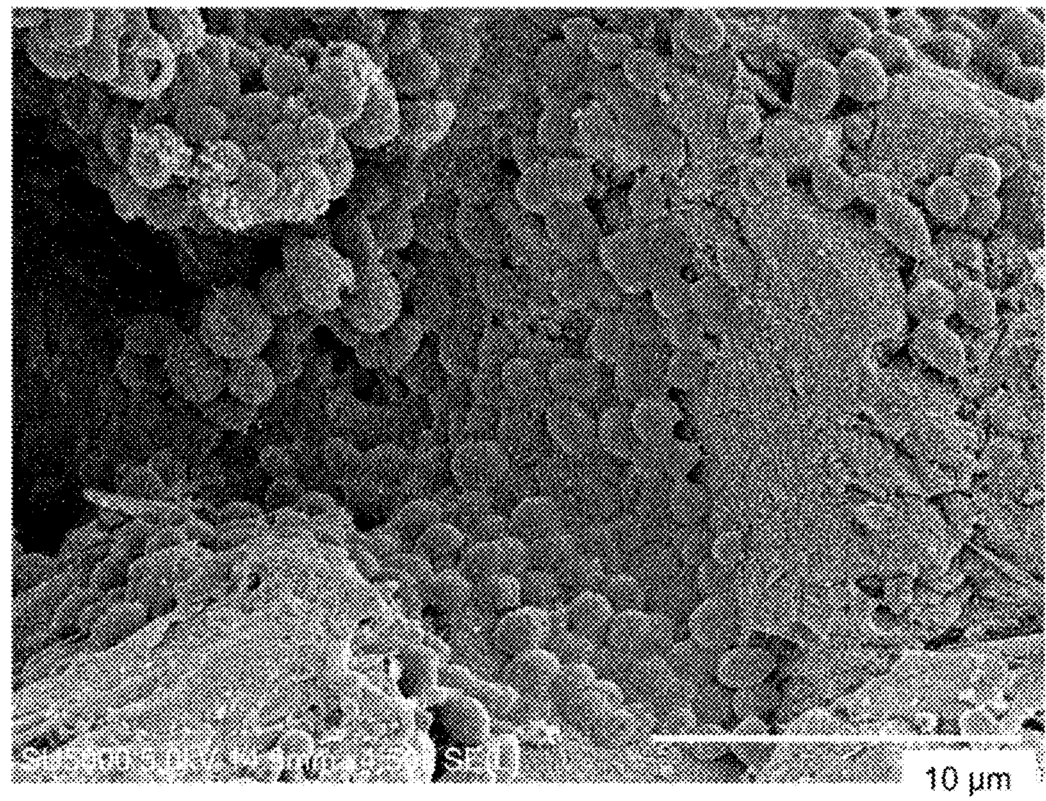

The consolidated sand samples were viewed under an SEM. From FIGS. 15A and 16A it can be clearly seen that there are $CaCO_3$ crystals precipitated within the pore spaces between sand grains. These crystals act as a cement to bind the sand grains together. Different morphologies of precipitated $CaCO_3$ crystals are observed, as shown in FIGS. 15B, 16B and 16C. Most formed a layered structure, in which layers of $CaCO_3$ crystals stack on top of each other. Spherical crystals were also detected in the second consolidated sample (FIG. 16C). Bacteria are also seen on the surface of sand grains or the precipitated $CaCO_3$ (FIGS. 15C and 16A).

Elements present in the consolidated sample were identified using EDS. EDS scans from the selected crystals, presented in FIG. 17, show a high amount of calcium (Ca), which is very likely to be $CaCO_3$. The gold peak seen in the EDS spectrums is due to gold coating of samples before SEM imaging.

Conclusions

Sand grains were successfully consolidated through our two-step process: dissolution using AP-004 bacteria and recrystallization using an SP strain. SEM images showed the binding of sand grains by precipitated crystals.

The invention claimed is:

1. A method of forming a construction material from $CaCO_3$ and a particulate starting material, comprising:

(i) providing a combined mixture that includes a combination of the $CaCO_3$ and the particulate starting material;

(ii) enzymatically generating an acid in a first portion of the combined mixture, wherein the acid generation causes a local pH decrease in the first portion of the combined mixture, thereby locally dissolving at least a first portion of the $CaCO_3$ in the first portion of the combined mixture; and (iii) enzymatically generating a local pH increase in a second portion of the combined mixture while enzymatically generating the acid in the first portion of the combined mixture thereby causing at least a second portion of the $CaCO_3$ to precipitate and to bind together at least part of the particulate starting material and the precipitated $CaCO_3$;

wherein one or more reagents for enzymatically generating the local pH increase are present in the combined mixture.

2. The method of claim 1, wherein the enzymatic generation of the local pH increase is performed using a microorganism or a microbial extract which contains enzymes.

3. The method of claim 2, wherein the microorganism is a bacterium or the microbial extract is a bacterial extract.

4. The method of claim 1, wherein the enzymatic generation of the local pH decrease is performed under aerobic conditions.

5. The method of claim 1, wherein the acid is a carboxylic acid and the particulate starting material comprises aggregate.

6. The method of claim 5, wherein the carboxylic acid is lactic acid or acetic acid.

7. The method of claim 1, wherein all the reagents for enzymatically generating the local pH increase and for enzymatically generating the acid are present in the combined mixture.

8. The method of claim 3, wherein both the pH decrease of (ii) and the pH increase of (iii) are performed using the same microorganism or microbial extract.

9. The method of claim 3, wherein the bacterium is of the strain having NCIMB accession number 42600, or a mutant or derivative thereof.

10. The method of claim 2, wherein the pH decrease of (ii) is performed using a different microorganism or extract thereof than the microorganism.

11. The method of claim 1, wherein:

the one or more reagents include urea; and the particulate starting material comprises a plurality of aggregate particles.

12. The method of claim 1, wherein:

the enzymatically generating the local pH increase includes adjusting at least one of an amount of oxygen or an amount of sugar provided to the combined mixture.

13. The method of claim 1, wherein:

the enzymatically generating the local pH increase includes reducing an amount of sugar or reducing an amount of oxygen provided to the combined mixture.

14. A method of forming a construction material, comprising:

(i) providing a combined mixture that includes a combination of $CaCO_3$ and a particulate starting material;

(ii) enzymatically generating an acid in the combined mixture during a first time period, wherein the acid generation causes a pH decrease in the combined mixture, thereby dissolving at least a first portion of the $CaCO_3$ in the combined mixture; and (iii) enzymatically generating a pH increase in the combined mixture during a second time period thereby causing at least some of the first portion of the $CaCO_3$ to precipitate and to bind together at least part of the particulate starting material and the precipitated $CaCO_3$, wherein one or more reagents for enzymatically generating the pH increase or for enzymatically generating the acid are present in the combined mixture prior to enzymatically generating the acid in the combined mixture.

15. A method of manufacturing a construction material, comprising:

acquiring a combined mixture that includes a combination of $CaCO_3$ and a particulate starting material;

enzymatically generating an acid in a first portion of the combined mixture, wherein the acid generation causes a local pH decrease in the first portion of the combined mixture and causes at least a first portion of the $CaCO_3$ to be locally dissolved in the first portion of the combined mixture; and enzymatically generating a local pH increase in a second portion of the combined mixture while enzymatically generating the acid in the first portion of the combined mixture thereby causing at least a second portion of the $CaCO_3$ to precipitate and to bind together at least part of the particulate starting material and the precipitated $CaCO_3$, wherein one or more reagents for enzymatically generating the local pH increase are present in the combined mixture prior to enzymatically generating the acid in the first portion of the combined mixture.

16. The method of claim 15, wherein the enzymatic generation of the local pH increase is performed using a microorganism or a microbial extract which contains enzymes.

17. The method of claim 16, wherein the microorganism is a bacterium or the microbial extract is a bacterial extract.

18. The method of claim 15, wherein the acid is a carboxylic acid and the particulate starting material comprises aggregate.

19. The method of claim 18, wherein the carboxylic acid is lactic acid or acetic acid.

20. The method of claim 14, wherein the enzymatic generation of the pH increase is performed using a microorganism or a microbial extract which contains enzymes.

21. The method of claim 20, wherein the microorganism is a bacterium or the microbial extract is a bacterial extract.

22. The method of claim 14, wherein the acid is a carboxylic acid and the particulate starting material comprises aggregate.

23. The method of claim 22, wherein the carboxylic acid is lactic acid or acetic acid.

24. The method of claim 14, wherein the enzymatic generation of the pH decrease is performed under aerobic conditions.

25. The method of claim 14, wherein all the reagents for enzymatically generating the pH increase and for enzymatically generating the acid are present in the combined mixture.

26. The method of claim 14, wherein the pH increase of (iii) is generated by metabolizing the acid.

27. The method of claim 14, wherein the pH increase of (iii) is generated by enzymatically producing ammonia.

28. The method of claim 14, wherein the pH increase of (iii) is generated bu urea hydrolysis.

29. The method of claim 14, wherein the microorganism is able to produce acid at a pH of at least 8.5.

30. The method of claim 14, wherein the microorganism is a facultative anaerobe or an obligate anaerobe.

31. The method of claim 14, wherein both the pH decreases of (ii) and the pH increase of (iii) are performed using the same microorganism or microbial extract.

32. The method of claim 14, wherein the pH decrease of (ii) is performed using a different microorganism or extract thereof than the microorganism or extract thereof of (iii).

33. The method of claim 14, wherein the pH decrease of (ii) or the pH increase of (iii) is performed using an isolated and purified or commercially acquired enzyme.

34. The method of claim 14, wherein the one or more reagents for enzymatically generating the pH increase and the one or more reagents for enzymatically generating the acid are present in the combined mixture prior to enzymatically generating the acid in the combined mixture.

35. The method of claim 14, wherein the acid is acetic acid.

36. A method of forming a construction material, comprising:

(i) providing a combined mixture that includes a combination of $CaCO_3$ and a particulate starting material;

(ii) enzymatically generating an acid in the combined mixture during a first time period, wherein the acid generation causes a local pH decrease in the combined mixture, thereby locally dissolving at least a first portion of the $CaCO_3$ in the combined mixture; and iii) enzymatically generating a local pH increase in the combined mixture during a second time period thereby causing at least some of the first portion of the $CaCO_3$ to precipitate and to bind together at least part of the particulate starting material and the precipitated $CaCO_3$, wherein one or more reagents for enzymatically generating the local pH increase and for enzymatically generating the acid are present in the combined mixture prior to enzymatically generating the acid in the combined mixture.

* * * * *